(12) United States Patent
Moon

(10) Patent No.: US 11,401,557 B2
(45) Date of Patent: Aug. 2, 2022

(54) BLADDER CANCER DETECTION USING MICROSATELLITE ANALYSIS IN PAIRED BUCCAL SWAB AND URINE SAMPLES

(71) Applicant: BCD INNOVATIONS, Lutherville, MD (US)

(72) Inventor: Chulso Moon, Lutherville, MD (US)

(73) Assignee: HJM FOUNDATION CORPORATION, Lutherville, MD (US)

( * ) Notice: Subject to any disclaimer, the term of this patent is extended or adjusted under 35 U.S.C. 154(b) by 179 days.

(21) Appl. No.: 16/060,620

(22) PCT Filed: Oct. 21, 2016

(86) PCT No.: PCT/US2016/058229
§ 371 (c)(1),
(2) Date: Jun. 8, 2018

(87) PCT Pub. No.: WO2017/099893
PCT Pub. Date: Jun. 15, 2017

(65) Prior Publication Data
US 2019/0112667 A1    Apr. 18, 2019

Related U.S. Application Data

(60) Provisional application No. 62/264,504, filed on Dec. 8, 2015.

(51) Int. Cl.
C12Q 1/68     (2018.01)
C12P 19/34    (2006.01)
C12Q 1/6886   (2018.01)
G16H 50/20    (2018.01)

(52) U.S. Cl.
CPC .......... *C12Q 1/6886* (2013.01); *G16H 50/20* (2018.01); *C12Q 2600/156* (2013.01); *C12Q 2600/16* (2013.01)

(58) Field of Classification Search
CPC ............ C12Q 1/6886; C12Q 2600/156; C12Q 2600/16; G16H 50/20
See application file for complete search history.

(56) References Cited

U.S. PATENT DOCUMENTS

| | | |
|---|---|---|
| 5,929,227 A | 7/1999 | Glazer et al. |
| 2002/0051974 A1 | 5/2002 | Dodge et al. |
| 2003/0113758 A1 | 6/2003 | Oudet et al. |
| 2009/0286236 A1 | 11/2009 | Sidransky |

FOREIGN PATENT DOCUMENTS

| WO | WO 2011/133935 A2 | 10/2011 |
|---|---|---|
| WO | 2015075027 A1 | 5/2015 |

OTHER PUBLICATIONS

Guillaume Legrand et al, "Prevalence and spectrum of microsatellite alterations in nonmuscle invasive bladder cancers". Am J Cancer Res 2011;1(5):595-603 (Year: 2011).*
Igor L. Medintz "Loss of Heterozygosity Assay for Molecular Detection of Cancer Using Energy-transfer Primers and Capillary Array Electrophoresis" Genome Research 10:1211-1218 (Year: 2000).*
Rolf I. Skotheim, et al, "Evaluation of loss of heterozygosity/allelic imbalance scoring in tumor DNA" Cancer Genetics and Cytogenetics 127 (2001) 64-70 (Year: 2001).*
Urs Hasse et al. "Clonal Loss of Heterozygosity in Microdissected Hodgkin and Reed-Sternberg Cells" Journal of the National Cancer Institute, vol. 91, No. 18, Sep. 15, 1999. (Year: 1999).*
Halachmi, et al., Molecular Diagnosis and Staging of Bladder Cancer, vol. 1, No. 4, Winter 1997, ISSN: 1091-5362; pp. 309-314.
Han, et al., The use of molecular diagnostics in bladder cancer, Urologic Oncology 5, 2000, pp. 87-92.
Anonymous: "Detection of Bladder Cancer by Microsatellite Analysis (MSA) of Urinary Sediment: Multi-Institutional Study," ICH GCP, Feb. 27, 2009 Clinical Trial NCT00095589—Results of this trial not yet available:See https://clinicaltrials.gov/ct2/show/NCT00095589.
Bartoletti R. et al., "Multiplex polymerase chain reaction for microsatellite analysis of urine sediment cells: A rapid and inexpensive method for diagnosing and monitoring superficial transitional bladder cell carcinoma," Journal of Urology, vol. 175, No. 6, Jun. 1, 2006, pp. 2032-2037.
"Relative fluorescent quantitation on capillary electrophoresis systems: screening for loss of heterozygosity in tumor samples on the Applied Biosystems 3130 Series Genetic Analyzers With GeneMapper Software v.3.7" Dec. 31, 2004.
Schoenberg, Mark P. et al., "Detecton of bladder cancer by microsatellite analysis (MSA) of urinary sediment: multi-institutional study grant number (U013A84968) EDRN Validation Study," Jul. 17, 2008, pp. 8, 9, 23.
Schneider A et al., "Evaluation of microsatellite analysis in urine sediment for diagnosis of bladder cancer," Cancer Research, American Association For Cancer Research, vol. 60, No. 16, Aug. 15, 2000, pp. 4617-4622.

* cited by examiner

*Primary Examiner* — Stephen T Kapushoc
(74) *Attorney, Agent, or Firm* — BakerHostetler

(57) ABSTRACT

Methods are described for the efficient and accurate detection of bladder cancer. In particular, the method utilizes microsatellite analysis of bladder cancer markers to determine the presence of loss of heterozygosity or microsatellite instability using matched buccal swab and urine samples from a patient. In some cancer marker panels, detected loss of heterozygosity or microsatellite instability in two markers can be indicative of bladder cancer.

24 Claims, 15 Drawing Sheets
Specification includes a Sequence Listing.

| DONOR # | URINE LOT # | SWAB LOT # | GENDER | AGE | DIAGNOSIS | MEDICATIONS | RACE | SMOKING/ALCOHOL USE |
|---|---|---|---|---|---|---|---|---|
| 1 | BRH777321 | BRH777326 | MALE | 70 | BLADDER CANCER, UROTHELIAL DYSPLASIA | LIPITOR 20mg, ASPIRIN 325mg | CAUCASIAN | NEVER SMOKER, NO ALCOHOL USE |
| 2 | BRH777322 | BRH777327 | MALE | 73 | BLADDER CANCER | DICLOFENAC, GABAPENTIN 600mg, ASPIRIN 81mg, PAXIL | CAUCASIAN | FORMER SMOKER, QUIT (1983) SMOKES CIGARS, SOCIAL ALCOHOL USE |
| 3 | BRH777323 | BRH777328 | MALE | 64 | BLADDER CANCER, TYPE 1 DIABETES | FLOMAX, ANAPRIL, LANTUS, SIMVASTIN, LOPRESSOR, VITAMIN D, NIACIN, OMEGA 3 | CAUCASIAN | NEVER SMOKER, SOCIAL ALCOHOL USE |
| 4 | BRH777324 | BRH777329 | FEMALE | 82 | BLADDER CANCER | METOPROLOL 25mg, CLOPIDOGREL 37.5mg, SIMVASTATIN 20mg, AMLODIPINE 5mg, CILOSTAZOL 100mg, ASPIRIN 81mg, MULTIVITAMIN | CAUCASIAN | 70 YEARS SMOKING, NO ALCOHOL USE |
| 5 | BRH777325 | BRH777330 | MALE | 77 | BLADDER CANCER | ACTOS 15mg, URIBEL 118mg, GLIPIZIDE 5mg, JANUVIA 50mg, CLONIDINE HYDROCHLORIDE 0.1mg, ALLOPURINOL 100mg, AMLODIPINE 5mg, CARVEDILOL 25mg, ATORVASTATIN 10mg | CAUCASIAN | FORMER SMOKER, NO ALCOHOL USE |

FIG. 5

FILE NAME OF SOURCE DATA  
SPECIMEN ID: N1 / N1  
BLOOD: BRH769667A  
URINE: BRH769882

| MARKER | LOWER LIMIT | UPPER LIMIT | RATIO 1 | DETERMINATION | HOMOZYGOUS | PHR >40%? | COMMENT (BLOOD ALLELES) | PH SUFFICIENT FOR HOMOZYOUS? | COMMENT (URINE ALLELES) |
|---|---|---|---|---|---|---|---|---|---|
| D4S243 | 0.75 | 1.31 | NONE | NON-INFORMATIVE | HOMOZYGOUS | N/A | NONE | YES | NONE |
| FGA | 0.79 | 1.23 | 0.81 | NEGATIVE | NONE | YES | NONE | N/A | NONE |
| D9S747 | 0.80 | 1.24 | 1.16 | NEGATIVE | NONE | YES | NONE | N/A | NONE |
| D17S654 | 0.80 | 1.26 | 1.06 | NEGATIVE | NONE | YES | NONE | N/A | NONE |
| D17S695 | 0.78 | 1.25 | 1.00 | NEGATIVE | NONE | YES | NONE | N/A | NONE |
| MBP | 0.86 | 1.21 | 1.07 | NEGATIVE | NONE | YES | NONE | N/A | NONE |
| MBPA | 0.86 | 1.31 | 1.09 | NEGATIVE | NONE | YES | NONE | N/A | NONE |
| D16S310 | 0.78 | 1.39 | 0.97 | NEGATIVE | NONE | YES | NONE | N/A | NONE |
| D9S162 | 0.80 | 1.23 | NONE | NON-INFORMATIVE | HOMOZYGOUS | N/A | NONE | YES | NONE |
| TH01 | 0.89 | 1.21 | NONE | NON-INFORMATIVE | HOMOZYGOUS | N/A | NONE | YES | NONE |
| IFN-A | 0.85 | 1.24 | NONE | NON-INFORMATIVE | HOMOZYGOUS | N/A | NONE | YES | NONE |
| D21S1245 | 0.77 | 1.20 | NONE | NON-INFORMATIVE | HOMOZYGOUS | N/A | NONE | YES | NONE |
| D20S48 | 0.81 | 1.21 | 0.97 | NEGATIVE | NONE | YES | NONE | N/A | NONE |
| D9S171 | 0.81 | 1.20 | 0.99 | NEGATIVE | NONE | YES | NONE | N/A | NONE |
| D16S476 | 0.89 | 1.21 | NONE | NON-INFORMATIVE | HOMOZYGOUS | N/A | NONE | YES | NONE |

FIG. 6A

| FILE NAME OF SOURCE DATA | | | | | | | | | | |
|---|---|---|---|---|---|---|---|---|---|---|
| SPECIMEN ID | | | | | | | | | | |
| BLOOD | N2 | | | | | | | | | |
| URINE | N2 | | | | | | | | | |
| | BRH769888A | | | | | | | | | |
| | BRH769883 | | | | | | | | | |
| MARKER | LOWER LIMIT | UPPER LIMIT | RATIO 1 | DETERMINATION | HOMOZYGOUS? | PHR >40%? | COMMENT (BLOOD ALLELES) | PH SUFFICIENT FOR HOMOZYOUS? | COMMENT (URINE ALLELES) |
| D4S243 | 0.68 | 1.33 | 0.94 | NEGATIVE | NONE | YES | NONE | N/A | NONE |
| FGA | 0.60 | 1.43 | 1.06 | NEGATIVE | NONE | YES | NONE | N/A | NONE |
| D9S747 | 0.63 | 1.42 | 0.69 | NEGATIVE | NONE | YES | NONE | N/A | NONE |
| D17S654 | 0.71 | 1.36 | 0.98 | NEGATIVE | NONE | YES | NONE | N/A | NONE |
| D17S695 | 0.49 | 1.61 | 1.06 | NEGATIVE | NONE | YES | NONE | N/A | NONE |
| MBP | 0.63 | 1.45 | 0.77 | NEGATIVE | NONE | YES | NONE | N/A | NONE |
| MBPA | 0.71 | 1.37 | 1.06 | NEGATIVE | NONE | YES | NONE | N/A | NONE |
| D16S310 | 0.60 | 1.34 | 1.33 | NEGATIVE | NONE | YES | NONE | N/A | NONE |
| D9S162 | 0.51 | 1.53 | NONE | NON-INFORMATIVE | HOMOZYGOUS | N/A | NONE | YES | NONE |
| TH01 | 0.46 | 1.53 | NONE | NON-INFORMATIVE | HOMOZYGOUS | N/A | NONE | YES | NONE |
| IFN-A | 0.68 | 1.43 | NONE | NON-INFORMATIVE | HOMOZYGOUS | N/A | NONE | YES | PEAK HEIGHT >5000 |
| D21S1245 | 0.58 | 1.42 | 1.03 | NEGATIVE | NONE | YES | NONE | N/A | NONE |
| D20S48 | 0.62 | 1.46 | 0.92 | NEGATIVE | NONE | YES | NONE | N/A | NONE |
| D9S171 | 0.72 | 1.36 | 0.89 | NEGATIVE | NONE | YES | NONE | N/A | NONE |
| D16S476 | 0.54 | 1.65 | 0.93 | NEGATIVE | NONE | YES | NONE | N/A | NONE |

*FIG. 6B*

| MARKER | LOWER LIMIT | UPPER LIMIT | RATIO 1 | DETERMINATION | HOMOZYGOUS? | PHR >40%? | COMMENT (BLOOD ALLELES) | PH SUFFICIENT FOR HOMOZYOUS? | COMMENT (URINE ALLELES) |
|---|---|---|---|---|---|---|---|---|---|
| FILE NAME OF SOURCE DATA | | | N3 | | | | | | |
| SPECIMEN ID | | | N3 | | | | | | |
| BUCCAL | | | BRH769889A | | | | | | |
| URINE | | | BRH769884 | | | | | | |
| D4S243 | 0.68 | 1.33 | 1.08 | NEGATIVE | NONE | YES | NONE | N/A | NONE |
| FGA | 0.6 | 1.43 | 0.83 | NEGATIVE | NONE | YES | NONE | N/A | NONE |
| D9S747 | 0.63 | 1.42 | 1.18 | NEGATIVE | NONE | YES | NONE | N/A | NONE |
| D17S654 | 0.71 | 1.36 | 1.00 | NEGATIVE | NONE | YES | NONE | N/A | NONE |
| D17S695 | 0.49 | 1.61 | 1.46 | NEGATIVE | NONE | YES | NONE | N/A | NONE |
| MBP | 0.63 | 1.45 | 1.11 | NEGATIVE | NONE | YES | NONE | N/A | NONE |
| MBPA | 0.71 | 1.37 | NONE | NON-INFORMATIVE | HOMOZYGOUS | N/A | NONE | YES | NONE |
| D16S310 | 0.6 | 1.34 | 0.93 | NEGATIVE | NONE | YES | NONE | N/A | NONE |
| D9S162 | 0.51 | 1.53 | 0.81 | NEGATIVE | NONE | YES | NONE | N/A | NONE |
| THO1 | 0.46 | 1.53 | 1.08 | NEGATIVE | NONE | YES | NONE | N/A | NONE |
| IFN-A | 0.68 | 1.43 | 1.21 | NEGATIVE | NONE | YES | NONE | N/A | NONE |
| D21S1245 | 0.58 | 1.42 | NONE | NON-EVALUABLE | HOMOZYGOUS | N/A | #DIV/0! | NO | PEAK HEIGHT INSUFFICIENT |
| D20S48 | 0.62 | 1.46 | NONE | NON-INFORMATIVE | HOMOZYGOUS | YES | PEAK HEIGHT INSUFFICIENT | YES | NONE |
| D8S171 | 0.72 | 1.36 | 1.12 | NEGATIVE | NONE | YES | NONE | N/A | NONE |
| D16S476 | 0.54 | 1.65 | 1.23 | NEGATIVE | NONE | YES | NONE | N/A | NONE |

*FIG. 6C*

| MARKER | FILE NAME OF SOURCE DATA | | | | | | | |
|---|---|---|---|---|---|---|---|---|
| | SPECIMEN ID | | N4 | | | | | |
| | BLOOD | | N4 | | | | | |
| | URINE | | BRH769880A | | | | | |
| | | | BRH769885 | | | | | |
| | LOWER LIMIT | UPPER LIMIT | RATIO 1 | DETERMINATION | HOMOZYGOUS? | PHR >40%? | COMMENT (BLOOD ALLELES) | PH SUFFICIENT FOR HOMOZYGOUS? | COMMENT (URINE ALLELES) |
| D4S243 | 0.68 | 1.33 | 0.84 | NEGATIVE | NONE | YES | NONE | N/A | NONE |
| FGA | 0.60 | 1.43 | 0.67 | NEGATIVE | NONE | YES | NONE | N/A | NONE |
| D9S747 | 0.63 | 1.42 | 1.07 | NEGATIVE | NONE | YES | NONE | N/A | NONE |
| D17S654 | 0.71 | 1.36 | NONE | NON-INFORMATIVE | HOMOZYGOUS | N/A | NONE | YES | NONE |
| D17S695 | 0.49 | 1.61 | 0.93 | NON-EVALUABLE | NONE | NO | NONE | N/A | NONE |
| MBP | 0.63 | 1.45 | 1.15 | NEGATIVE | NONE | YES | NONE | N/A | NONE |
| MBPA | 0.71 | 1.37 | 1.06 | NEGATIVE | NONE | YES | NONE | N/A | NONE |
| D16S310 | 0.60 | 1.34 | 1.08 | NEGATIVE | NONE | YES | NONE | N/A | NONE |
| D9S162 | 0.51 | 1.53 | NONE | NON-INFORMATIVE | HOMOZYGOUS | N/A | NONE | YES | NONE |
| TH01 | 0.46 | 1.53 | 1.04 | NEGATIVE | NONE | YES | NONE | N/A | NONE |
| IFN-A | 0.68 | 1.43 | 1.04 | NEGATIVE | NONE | YES | NONE | N/A | NONE |
| D21S1245 | 0.58 | 1.42 | 1.17 | NEGATIVE | NONE | YES | NONE | N/A | NONE |
| D20S48 | 0.62 | 1.46 | 1.20 | NEGATIVE | NONE | YES | NONE | N/A | NONE |
| D9S171 | 0.72 | 1.36 | 1.01 | NEGATIVE | NONE | YES | NONE | N/A | NONE |
| D16S476 | 0.54 | 1.65 | 0.99 | NEGATIVE | NONE | YES | NONE | N/A | NONE |

FIG. 6D

FILE NAME OF SOURCE DATA
SPECIMEN ID
BUCCAL: N5
URINE: N5
BRH769891A
BRH769886

| MARKER | LOWER LIMIT | UPPER LIMIT | RATIO 1 | DETERMINATION | HOMOZYGOUS? | PHR >40%? | COMMENT (BUCCAL ALLELES) | PH SUFFICIENT FOR HOMOZYGOUS? | COMMENT (URINE ALLELES) |
|---|---|---|---|---|---|---|---|---|---|
| D4S243 | 0.68 | 1.33 | 0.99 | NEGATIVE | NONE | YES | NONE | N/A | NONE |
| FGA | 0.6 | 1.43 | 1.01 | NEGATIVE | NONE | YES | NONE | N/A | NONE |
| D9S747 | 0.63 | 1.42 | NONE | NON-INFORMATIVE | HOMOZYGOUS | N/A | NONE | YES | PEAK HEIGHT>5000 |
| D17S654 | 0.71 | 1.36 | 1.29 | NEGATIVE | NONE | YES | NONE | N/A | NONE |
| D17S695 | 0.49 | 1.61 | NONE | NON-INFORMATIVE | HOMOZYGOUS | N/A | NONE | YES | NONE |
| MBP | 0.63 | 1.45 | 0.97 | NEGATIVE | NONE | YES | NONE | N/A | NONE |
| MBPA | 0.71 | 1.37 | 0.98 | NEGATIVE | NONE | YES | NONE | N/A | NONE |
| D16S310 | 0.6 | 1.34 | NONE | NON-INFORMATIVE | HOMOZYGOUS | N/A | NONE | YES | NONE |
| D9S162 | 0.51 | 1.53 | NONE | NON-INFORMATIVE | HOMOZYGOUS | N/A | NONE | YES | NONE |
| THO1 | 0.46 | 1.53 | 0.61 | NEGATIVE | NONE | YES | NONE | N/A | NONE |
| IFN-A | 0.68 | 1.43 | NONE | NON-INFORMATIVE | HOMOZYGOUS | N/A | NONE | YES | NONE |
| D21S1245 | 0.58 | 1.42 | 1.23 | NEGATIVE | NONE | YES | NONE | N/A | NONE |
| D20S48 | 0.62 | 1.46 | 0.73 | NEGATIVE | NONE | YES | NONE | N/A | NONE |
| D9S171 | 0.72 | 1.36 | NONE | NON-INFORMATIVE | HOMOZYGOUS | N/A | NONE | YES | NONE |
| D16S476 | 0.54 | 1.65 | 0.93 | NEGATIVE | NONE | YES | NONE | N/A | NONE |

*FIG. 6E*

| MARKER | FILE NAME OF SOURCE DATA | | | | | | | | | |
|---|---|---|---|---|---|---|---|---|---|---|
| | SPECIMEN ID | | | | | | | | | |
| | BUCCAL | C1 | | | | | | | | |
| | URINE | C1 | | | | | | | | |
| | LOWER LIMIT | UPPER LIMIT | RATIO 1 | DETERMINATION | CONFIRMATION | HOMOZYGOUS? | PHR >40%? | COMMENT (BUCCAL ALLELES) | PH SUFFICIENT FOR HOMOZYOUS? | COMMENT (URINE ALLELES) |
| D4S243 | 0.75 | 1.31 | BRH777326 | | | | | | | |
| FGA | 0.79 | 1.23 | BRH777321 | | | | | | | |
| D9S747 | 0.80 | 1.24 | 0.99 | NEGATIVE | NEGATIVE | NONE | YES | NONE | N/A | NONE |
| D17S654 | 0.80 | 1.26 | 1.22 | NEGATIVE | NEGATIVE | NONE | YES | NONE | N/A | NONE |
| D17S695 | 0.78 | 1.25 | 0.99 | NEGATIVE | NEGATIVE | NONE | YES | NONE | N/A | NONE |
| | | | 1.07 | NEGATIVE | NEGATIVE | NONE | YES | NONE | N/A | NONE |
| | | | NONE | NON-INFORMATIVE | NON-INFORMATIVE | HOMOZYGOUS | N/A | NONE | YES | NONE |
| MBP | 0.86 | 1.21 | 0.80 | POSITIVE | POSITIVE | NONE | YES | NONE | N/A | NONE |
| MBPA | 0.86 | 1.31 | 1.12 | NEGATIVE | NEGATIVE | NONE | YES | NONE | N/A | NONE |
| D16S310 | 0.78 | 1.39 | NONE | NON-INFORMATIVE | NON-INFORMATIVE | HOMOZYGOUS | N/A | NONE | YES | NONE |
| D9S162 | 0.80 | 1.23 | 1.03 | NEGATIVE | NEGATIVE | NONE | YES | NONE | N/A | NONE |
| THO1 | 0.89 | 1.21 | 1.01 | NEGATIVE | NEGATIVE | NONE | YES | NONE | N/A | NONE |
| IFN-A | 0.85 | 1.24 | 1.02 | NEGATIVE | NEGATIVE | NONE | YES | NONE | N/A | NONE |
| D21S1245 | 0.77 | 1.20 | 0.99 | NEGATIVE | NEGATIVE | NONE | YES | NONE | N/A | NONE |
| D20S48 | 0.81 | 1.21 | 1.38 | POSITIVE | POSITIVE | NONE | YES | NONE | N/A | NONE |
| D9S171 | 0.81 | 1.20 | 1.00 | NEGATIVE | NEGATIVE | NONE | YES | NONE | N/A | NONE |
| D16S476 | 0.89 | 1.21 | 0.94 | NEGATIVE | NEGATIVE | NONE | YES | NONE | N/A | NONE |

*FIG. 6F*

| FILE NAME OF SOURCE DATA | | | | | | | | | |
|---|---|---|---|---|---|---|---|---|---|
| SPECIMEN ID | | | MSA C2 | | | | | | |
| BUCCAL | | | C2 | | | | | | |
| URINE | | | BRH777327 | | | | | | |
| | | | BRH777322 | | | | | | |
| MARKER | LOWER LIMIT | UPPER LIMIT | RATIO 1 | DETERMINATION | CONFIRMATION | HOMOZYGOUS? | PHR >40%? | COMMENT (BUCCAL ALLELES) | PH SUFFICIENT FOR HOMOZYOUS? | COMMENT (URINE ALLELES) |
| D4S243 | 0.75 | 1.31 | 1.03 | NEGATIVE | NEGATIVE | NONE | YES | NONE | N/A | NONE |
| FGA | 0.79 | 1.23 | 0.91 | NEGATIVE | NEGATIVE | NONE | YES | NONE | N/A | NONE |
| D9S747 | 0.80 | 1.24 | NONE | NON-INFORMATIVE | NON-INFORMATIVE | HOMOZYGOUS | N/A | NONE | YES | NONE |
| D17S654 | 0.80 | 1.26 | NONE | NON-INFORMATIVE | NON-INFORMATIVE | HOMOZYGOUS | N/A | NONE | YES | NONE |
| D17S695 | 0.78 | 1.25 | 1.12 | NEGATIVE | NEGATIVE | NONE | YES | NONE | N/A | NONE |
| | | | | | | | | | | |
| MBP | 0.86 | 1.21 | 0.97 | NEGATIVE | NEGATIVE | NONE | YES | NONE | N/A | NONE |
| MBPA | 0.86 | 1.31 | NONE | NON-INFORMATIVE | NON-INFORMATIVE | HOMOZYGOUS | N/A | NONE | YES | NONE |
| D16S310 | 0.78 | 1.39 | 0.88 | NEGATIVE | NEGATIVE | NONE | YES | NONE | N/A | NONE |
| D9S162 | 0.80 | 1.23 | 0.87 | NEGATIVE | NEGATIVE | NONE | YES | NONE | N/A | NONE |
| THO1 | 0.89 | 1.21 | 1.01 | NEGATIVE | NEGATIVE | NONE | YES | NONE | N/A | NONE |
| IFN-A | 0.85 | 1.24 | 0.87 | NEGATIVE | NEGATIVE | NONE | YES | NONE | N/A | NONE |
| | | | | | | | | | | |
| D21S1245 | 0.77 | 1.20 | 1.79 | POSITIVE | MSI | NONE | NO | PEAK HEIGHT INSUFF. | N/A | NONE |
| D20S48 | 0.81 | 1.21 | 1.96 | POSITIVE | NEGATIVE | NONE | YES | NONE | N/A | NONE |
| D9S171 | 0.81 | 1.20 | NONE | NON-INFORMATIVE | NON-INFORMATIVE | HOMOZYGOUS | N/A | NONE | YES | NONE |
| D16S476 | 0.89 | 1.21 | NONE | NON-INFORMATIVE | NON-INFORMATIVE | HOMOZYGOUS | N/A | NONE | YES | NONE |

FIG. 6G

| MARKER | FILE NAME OF SOURCE DATA | | | | | | | | |
|---|---|---|---|---|---|---|---|---|---|
| | SPECIMEN ID | | | | | | | | |
| | BUCCAL | C3 | | | | | | | |
| | URINE | C3 | | | | | | | |
| | LOWER LIMIT | UPPER LIMIT | BRH777328 RATIO 1 | BRH777323 DETERMINATION | CONFIRMATION | HOMOZYGOUS? | PHR >40%? | COMMENT (BUCCAL ALLELES) | PH SUFFICIENT FOR HOMOZYOUS? | COMMENT (URINE ALLELES) |
| D4S243 | 0.75 | 1.31 | 1.21 | NEGATIVE | NEGATIVE | NONE | YES | NONE | N/A | NONE |
| FGA | 0.79 | 1.23 | 0.97 | NEGATIVE | NEGATIVE | NONE | YES | NONE | N/A | NONE |
| D9S747 | 0.80 | 1.24 | NONE | NON-INFORMATIVE | NON-INFORMATIVE | HOMOZYGOUS | N/A | NONE | YES | NONE |
| D17S654 | 0.80 | 1.26 | 1.07 | NEGATIVE | NEGATIVE | NONE | YES | NONE | N/A | NONE |
| D17S695 | 0.78 | 1.25 | 0.96 | NEGATIVE | NEGATIVE | NONE | YES | NONE | N/A | NONE |
| | | | | | | | | | | |
| MBP | 0.86 | 1.21 | 1.22 | POSITIVE | POSITIVE | NONE | YES | NONE | N/A | NONE |
| MBPA | 0.86 | 1.31 | NONE | NON-INFORMATIVE | NON-INFORMATIVE | HOMOZYGOUS | N/A | NONE | YES | NONE |
| D16S310 | 0.78 | 1.39 | 1.02 | NEGATIVE | NEGATIVE | NONE | YES | NONE | N/A | NONE |
| D9S162 | 0.80 | 1.23 | NONE | NON-INFORMATIVE | NON-INFORMATIVE | HOMOZYGOUS | N/A | NONE | YES | PEAK HEIGHT> |
| THO1 | 0.89 | 1.21 | 1.77 | POSITIVE | POSITIVE | NONE | YES | NONE | N/A | NONE |
| IFN-A | 0.85 | 1.24 | 1.69 | POSITIVE | POSITIVE | NONE | YES | NONE | N/A | NONE |
| | | | | | | | | | | |
| D21S1245 | 0.77 | 1.20 | NONE | NON-INFORMATIVE | NON-INFORMATIVE | HOMOZYGOUS | N/A | NONE | YES | NONE |
| D20S48 | 0.81 | 1.21 | 1.03 | NEGATIVE | NEGATIVE | NONE | YES | NONE | N/A | NONE |
| D9S171 | 0.81 | 1.20 | NONE | NON-INFORMATIVE | NON-INFORMATIVE | HOMOZYGOUS | N/A | NONE | YES | NONE |
| D16S476 | 0.89 | 1.21 | NONE | NON-INFORMATIVE | NON-INFORMATIVE | HOMOZYGOUS | N/A | NONE | YES | NONE |

*FIG. 6H*

| MARKER | FILE NAME OF SOURCE DATA SPECIMEN ID BUCCAL URINE LOWER LIMIT | UPPER LIMIT | C4 C4 BRH777329 BRH777324 RATIO 1 | DETERMINATION | CONFIRMATION | HOMOZYGOUS? | PHR >40%? | COMMENT (BUCCAL ALLELES) | PH SUFFICIENT FOR HOMOZYOUS? | COMMENT (URINE ALLELES) |
|---|---|---|---|---|---|---|---|---|---|---|
| D4S243 | 0.75 | 1.31 | NONE | NON-INFORMATIVE | NON-INFORMATIVE | HOMOZYGOUS | N/A | NONE | YES | NONE |
| FGA | 0.79 | 1.23 | 1.50 | POSITIVE | POSITIVE | HOMOZYGOUS | N/A | NONE | N/A | NONE |
| D9S747 | 0.80 | 1.24 | 0.38 | POSITIVE | POSITIVE | NONE | YES | NONE | N/A | NONE |
| D17S654 | 0.80 | 1.26 | 1.02 | NEGATIVE | NEGATIVE | NONE | YES | NONE | N/A | NONE |
| D17S695 | 0.78 | 1.25 | 1.04 | NEGATIVE | NEGATIVE | NONE | YES | NONE | N/A | NONE |
| MBP | 0.86 | 1.21 | NONE | NON-INFORMATIVE | NON-INFORMATIVE | HOMOZYGOUS | N/A | NONE | YES | NONE |
| MBPA | 0.86 | 1.31 | 1.24 | NEGATIVE | NEGATIVE | NONE | YES | NONE | N/A | NONE |
| D16S310 | 0.78 | 1.39 | 1.10 | NEGATIVE | NEGATIVE | NONE | YES | NONE | N/A | NONE |
| D8S162 | 0.80 | 1.23 | 3.97 | POSITIVE | POSITIVE | NONE | YES | NONE | N/A | NONE |
| TH01 | 0.89 | 1.21 | 0.79 | POSITIVE | POSITIVE | NONE | YES | NONE | N/A | NONE |
| IFN-A | 0.85 | 1.24 | 1.04 | NEGATIVE | NEGATIVE | NONE | YES | NONE | N/A | NONE |
| D21S1245 | 0.77 | 1.20 | 1.20 | POSITIVE | POSITIVE | NONE | YES | NONE | N/A | NONE |
| D20S48 | 0.81 | 1.21 | 0.96 | NEGATIVE | NEGATIVE | NONE | YES | NONE | N/A | NONE |
| D9S171 | 0.81 | 1.20 | 1.04 | NEGATIVE | NEGATIVE | NONE | YES | NONE | N/A | NONE |
| D16S476 | 0.89 | 1.21 | NONE | NON-INFORMATIVE | NON-INFORMATIVE | HOMOZYGOUS | N/A | NONE | YES | NONE |

*FIG. 6I*

FILE NAME OF SOURCE DATA
SPECIMEN ID
BUCCAL: C5
URINE: C5
BRH777330
BRH777325

| MARKER | LOWER LIMIT | UPPER LIMIT | RATIO 1 | DETERMINATION | CONFIRMATION | HOMOZYGOUS? | PHR >40%? | COMMENT (BUCCAL ALLELES) | PH SUFFICIENT FOR HOMOZYOUS? | COMMENT (URINE ALLELES) |
|---|---|---|---|---|---|---|---|---|---|---|
| D4S243 | 0.75 | 1.31 | 0.96 | NEGATIVE | NEGATIVE | NONE | YES | NONE | N/A | NONE |
| FGA | 0.79 | 1.23 | 0.87 | NEGATIVE | NEGATIVE | NONE | YES | NONE | N/A | NONE |
| D9S747 | 0.80 | 1.24 | NONE | NON-INFORMATIVE | MSI | HOMOZYGOUS | N/A | NONE | YES | NONE |
| D17S654 | 0.80 | 1.26 | 1.05 | NEGATIVE | NEGATIVE | NONE | YES | NONE | N/A | NONE |
| D17S695 | 0.78 | 1.25 | 1.20 | NEGATIVE | NEGATIVE | NONE | YES | NONE | N/A | NONE |
| MBP | 0.86 | 1.21 | 0.85 | POSITIVE | POSITIVE | NONE | YES | NONE | N/A | NONE |
| MBPA | 0.86 | 1.31 | 1.05 | NEGATIVE | NEGATIVE | NONE | YES | NONE | N/A | NONE |
| D16S310 | 0.78 | 1.39 | 0.81 | NEGATIVE | NEGATIVE | NONE | YES | NONE | N/A | NONE |
| D9S162 | 0.80 | 1.23 | 1.05 | NEGATIVE | NEGATIVE | NONE | YES | NONE | N/A | NONE |
| TH01 | 0.89 | 1.21 | 0.97 | NEGATIVE | NEGATIVE | NONE | YES | NONE | N/A | NONE |
| IFN-A | 0.85 | 1.24 | NONE | NON-INFORMATIVE | NON-INFORMATIVE | HOMOZYGOUS | N/A | NONE | YES | NONE |
| D21S1245 | 0.77 | 1.20 | 1.77 | NON-EVALUABLE | POSITIVE | NONE | YES | PEAK HEIGHT INSUFF. | N/A | NONE |
| D20S48 | 0.81 | 1.21 | 1.01 | NEGATIVE | NEGATIVE | NONE | YES | NONE | N/A | NONE |
| D9S171 | 0.81 | 1.20 | 1.14 | NEGATIVE | NEGATIVE | NONE | YES | NONE | N/A | NONE |
| D16S476 | 0.89 | 1.21 | 1.04 | NEGATIVE | NEGATIVE | NONE | YES | NONE | N/A | NONE |

FIG. 6J

BLADDER CANCER DETECTION USING MICROSATELLITE ANALYSIS IN PAIRED BUCCAL SWAB AND URINE SAMPLES

CROSS REFERENCE TO RELATED APPLICATIONS

This application is a continuation application of U.S. patent application Ser. No. 17/383,291 filed Jul. 22, 2021, which is a continuation application of U.S. patent application Ser. No. 16/060,620 filed Jun. 8, 2018, which is the National Stage Application of International Patent Application No. PCT/US2016/058229 filed Oct. 21, 2016, which claims priority to U.S. Provisional Patent Application No. 62/264,504, filed Dec. 8, 2015, the entire disclosures of which are hereby incorporated herein by reference in their entireties.

FIELD OF THE INVENTION

Disclosed herein are compositions and methods useful for detection of bladder cancer.

BACKGROUND OF THE INVENTION

Bladder cancer is the fourth and seventh most common malignancy in American men and women, respectively. Annually, 60,000 and 18,000 new cases of bladder cancer are diagnosed in American men and women, respectively. About 75% of patients have a superficial form of the disease, and 15% of these patients are at risk of the disease progressing to an invasive form. About 70% of patients with the superficial form of the disease experience disease recurrence within 10 years, with the majority of recurrences being detected within two years of the initial diagnoses. For these reason, patients with the superficial form of the disease require monitoring for disease progression and recurrence.

Currently, the standard of care for bladder cancer surveillance includes a cystoscopy and urinary cytology every three months for two years followed by annual cystoscopies, urinary cytologies, and radiographic evaluations of the upper urinary tract. However, this surveillance approach not optimal as the sensitivity and specificity for cytology is only 25-50% and 90-100%, respectively. While sensitivity of cystoscopy is higher (90-100%), it is an expensive procedure that requires intricate instrumentation and a sterile environment. And because of its invasive nature, the procedure has inherent risks of injury, complications, and infection.

Thus, there is a need for methods of detecting bladder cancer that are both sensitive and specific for the disease and that have less risk of complications compared to other detection methods. The disclosed methods and kits directed to these and other important needs.

SUMMARY OF THE INVENTION

To address, inter alia, the unmet needs described above, disclosed herein are methods for detecting loss of heterozygosity in a subject comprising amplifying a set of microsatellite markers from a bladder sample and a matched control sample to produce a set of amplification products, wherein the set of markers comprise FGA, D9S747, MBP, D9S162, TH01, IFN-A, D21S1245, and D20S48; detecting the amplification products; comparing the amplification products from the bladder sample and the amplification products from the matched control sample; and determining if loss of heterozygosity is present in any of the markers in the bladder sample.

Methods are also provided for detecting bladder cancer in a subject comprising amplifying a set of microsatellite markers from a bladder sample and a control sample using the primers described herein; detecting the reaction product; and determining if more than one of the microsatellite markers exhibits loss of heterozygosity or microsatellite instability in the bladder sample, wherein in at least two microsatellite markers exhibiting loss of heterozygosity or instability is indicative of bladder cancer.

Also disclosed herein are kits comprising primers having specific nucleic acid sequences and packaging for said primers.

BRIEF DESCRIPTION OF THE DRAWINGS

The summary, as well as the following detailed description, is further understood when read in conjunction with the appended drawings. For the purpose of illustrating the disclosed methods and kits, there are shown in the drawings exemplary embodiments of the methods and kits; however, the methods and kits are not limited to the specific embodiments disclosed. In the drawings:

FIG. 5 provides a summary of characteristics and associated sample numbers for study subjects having bladder cancer;

FIG. 6A shows the MSA profile for control subject N1;
FIG. 6B shows the MSA profile for control subject N2;
FIG. 6C shows the MSA profile for control subject N3;
FIG. 6D shows the MSA profile for control subject N4;
FIG. 6E shows the MSA profile for control subject N5;
FIG. 6F shows the MSA profile for bladder cancer subject C1;
FIG. 6G shows the MSA profile for bladder cancer subject C2;
FIG. 6H shows the MSA profile for bladder cancer subject C3;
FIG. 6I shows the MSA profile for bladder cancer subject C4; and
FIG. 6J shows the MSA profile for bladder cancer subject C5.

DETAILED DESCRIPTION OF ILLUSTRATIVE EMBODIMENTS

Figure 1:
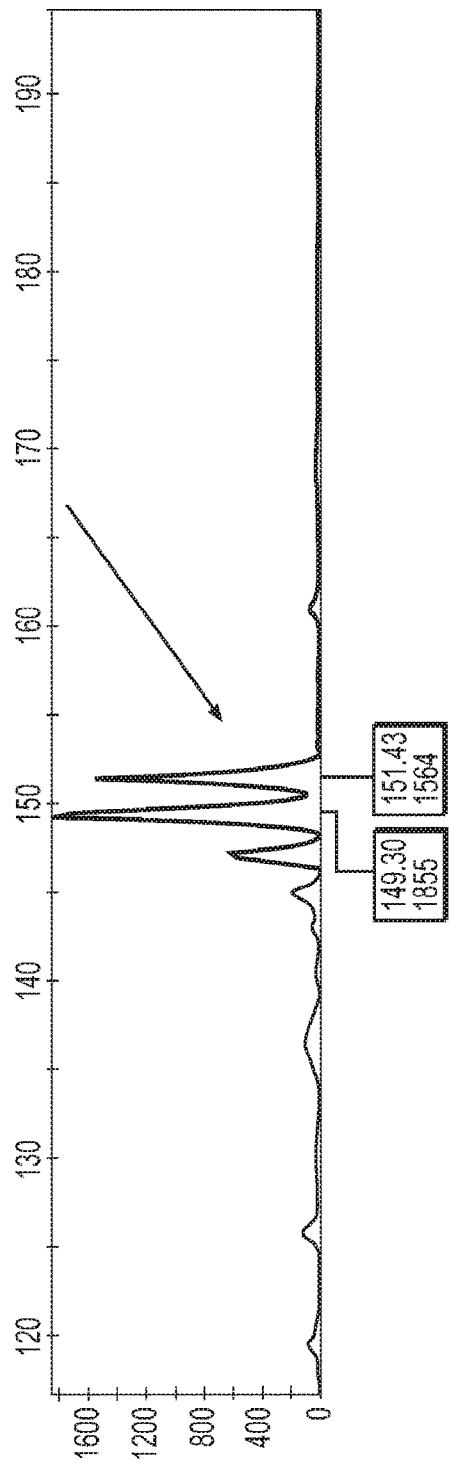
FIG. 1 illustrates LOH at the IFN-A locus.
Figure 1:
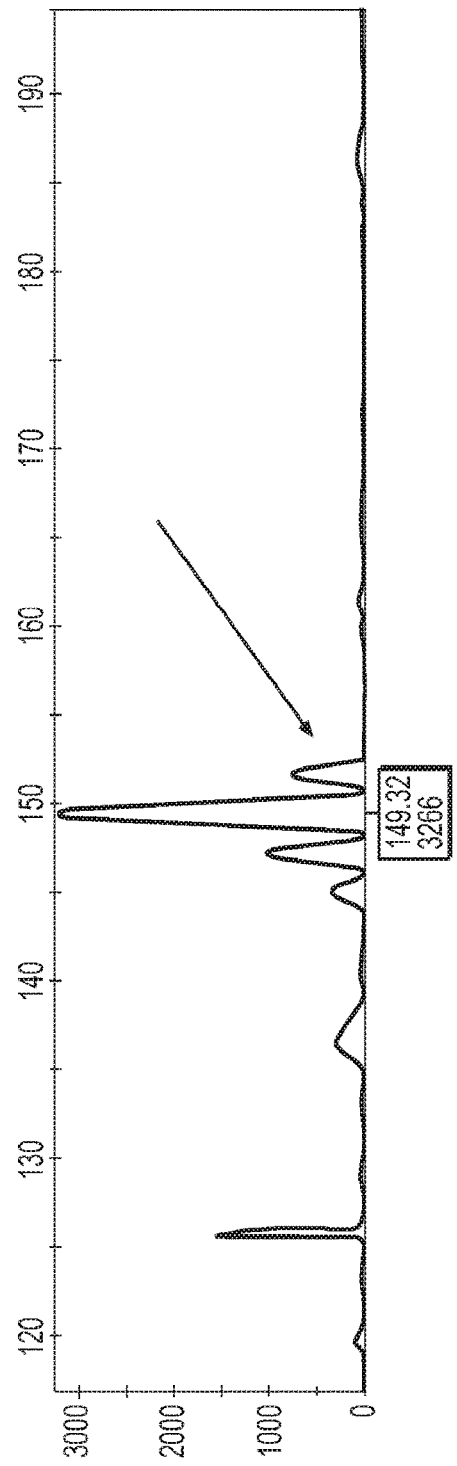

The disclosed methods and kits may be understood more readily by reference to the following detailed description taken in connection with the accompanying figures, which form a part of this disclosure. It is to be understood that the disclosed methods and kits are not limited to the specific methods and kits described and/or shown herein, and that the terminology used herein is for the purpose of describing particular embodiments by way of example only and is not intended to be limiting of the claimed methods and kits.

Unless specifically stated otherwise, any description as to a possible mechanism or mode of action or reason for improvement is meant to be illustrative only, and the disclosed methods and kits are not to be constrained by the correctness or incorrectness of any such suggested mechanism or mode of action or reason for improvement.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

When a range of values is expressed, another embodiment includes from the one particular value and/or to the other particular value. Further, reference to values stated in ranges include each and every value within that range. All ranges are inclusive and combinable. When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed methods and kits which are, for clarity, described herein in the context of separate embodiments, may also be provided in combination in a single embodiment. Conversely, various features of the disclosed methods and kits that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, "microsatellite," (used interchangeably with "simple sequence repeat" (SSR) and "short tandem repeat" (STR)) refers to segments of nucleic acids having contiguous repeats of a base unit consisting of two to six base pairs. Microsatellites are generally 100-400 base pairs in length. Thus, if the base unit of the microsatellite is 4 base pairs, there will be about 25 to 100 contiguous repeats of the base unit.

"Microsatellite instability" refers changes that occur to the nucleic acid sequence of microsatellites in a cell when the mismatch repair (MMR) is not functioning properly. The characteristic repeat units of a microsatellite are prone to errors caused by failure of DNA polymerases' inherent proof-reading capability to correct mismatches. Accumulation of insertions or deletions of nucleobases can lead to frameshift mutations that can have deleterious effects on protein expression. The MMR system can be viewed as a fail-safe system because those mismatch errors undetected by the DNA polymerase are corrected by the MMR. Mutations in the genes encoding the MMR system result in lack of surveillance of microsatellite replication and instability can result. Microsatellite instability occurring in tumor suppressor genes has been associated with cancer phenotypes.

The term "loss of heterozygosity," or LOH, refers to loss of a segment of DNA, most likely due to replication error in one chromosomal strand but not in the other. In some cancers, LOH can be particularly problematic if the lost genetic material encodes all or part of a tumor suppressor protein, cellular reproduction machinery, or other proteins necessary for the stable reproduction of cells. Although the remaining copy may be sufficient to prevent any deleterious effects caused by the lost allele, LOH can result in—or at least contribute to—a cancer phenotype if the remaining copy is insufficient to prevent deleterious effects or if the remaining copy is mutagenized such that the encoded protein does not function as a wildtype protein. LOH at a microsatellite allele may be associated with cancer because the remaining microsatellite allele, still susceptible to mutation—and especially so in a cell lacking a fully functional MMR system—may acquire further mutations or variations that result in a non-functioning protein. If the nonfunctioning protein is a tumor suppressor, there is a heightened risk of a cancer phenotype.

In addition to the approximately 80,000 new cases of bladder cancer diagnosed each year, approximately 12,000 men and 4,500 women dies from the disease annually. Because of the prevalence of the disease in the United States and abroad, much research has been undertaken to identify genetic components that may be contributing or otherwise indicative of the disease. This research has identified numerous tumor markers associated—in some capacity—with the disease, and in the past decade, several tumor markers have been incorporated into in vitro diagnostic assays for bladder tumor detection. Currently, BTA™, BTA™ Stat, FDP™, and NMP-22™ have been cleared by the Food and Drug Administration (FDA) as adjuncts to cystology and cytology, and these tests are usually antibody-mediated detection of tumor markers. Sensitivity and selectivity profiles for these assays suggest that although these marker detection methods may augment contemporary invasive detection procedures, their sensitivity and selectivity profiles suggest that they cannot be relied on without a companion diagnostic (Halachmi et al., Molecular Urology, 1(4):309-314 (1997); Han and Schoenberg, Urologic Oncology, 5(3):87-92 (2000)). For example, sensitivity of the BLA Stat test, depending on the stage of disease, can be as low as 51% and as low as 42% for stage 1 cancers.

The present invention, in contrast, is a method of detecting bladder cancer without the need for invasive techniques or a combinatorial approach to diagnosis. More specifically, the present invention detects LOH or MSI in bladder cells by analyzing a specific set of microsatellite markers from a bladder specimen, wherein LOH detected at two markers in a bladder sample is indicative of disease. The disease, in some embodiments of the present invention, is bladder cancer.

While no invasive techniques are necessary to obtain test specimens, the invention is not limited to only non-invasively derived samples. Samples obtained from biopsy, surgery, and even autopsy can be used to detect bladder cancer using the presently described techniques. In some aspects of the present invention, the bladder sample can be a urine sample, and in other aspects, the bladder sample can be a bladder biopsy sample. In some embodiments of the present invention, a matched control sample is blood, blood serum, buccal cells, hair follicle, saliva, sebum, skin, sweat, or tears. In some aspects, the matched control sample is buccal cells.

Microsatellites can be used as markers to detect, diagnose, and/or study diseases when the microsatellites associated with a particular disease. The present invention discloses a method of detecting changes in a panel of microsatellite markers. In order to detect these markers, nucleic acid from a bladder specimen must be isolated. Amplifying of a microsatellite allows for one skilled in the art to detect the presence of, absence of, or changes to the microsatellite. The microsatellite is flanked by sequences that can be used to design primers for use in amplifying the microsatellite. Thus, in some aspects of the present invention, each marker is amplified using a pair of primers. Table 1 recites the primers used for each marker amplified in one embodiment of the present invention.

Amplification of nucleic acids is accomplished using any technique capable of amplifying nucleic acids, such as isothermal amplification reactions, which amplify nucleic acids at a substantially isothermal temperature, or polymerase chain reactions (PCR), which utilize multiple cycles of different temperatures to denaturate template nucleic acids, anneal primers, and extend a nascent nucleic acid strand. PCR reactions include, but are not limited to, traditional PCR, real time (RT) PCR, and qualitative PCR (qPCR). Any amplification protocol that allows for the discrimination of amplified nucleic acids based on size is contemplated in the present invention. In one embodiment of the present invention, a microsatellite marker is amplified from nucleic acids obtained from a urine sample and from a buccal sample. The resulting amplified nucleic acids will have an expected length, and any derivation from that expected length, including the complete absence of an amplified product, may signal microsatellite instability or loss of heterozygosity.

One embodiment of the present invention provides a method for detecting LOH in a subject comprising amplifying microsatellite markers from a bladder sample and a matched control sample to produce amplification products, wherein the markers comprise FGA, D9S747, MBP, D9S162, TH01, IFN-A, D21S1245, and D20S48; detecting the amplification products; comparing the amplification products from the bladder sample and the amplification products from the matched control sample; and determining if loss of heterozygosity is present in any of the markers in the bladder sample.

Amplified nucleic acids can be resolved using molecular methods known in the art including, but not limited to, agarose gel electrophoresis, capillary electrophoresis, and high pressure liquid chromatography. When comparing a single amplified product from a bladder sample and a single amplified product from a control sample, agarose gel electrophoresis allows for a visual determination if the samples possess the marker nucleic acid. Capillary electrophoresis also allows for the resolution of differently sized amplification product in an automated fashion, and this method is especially well suited for resolving multiple amplification products in a single capillary.

Some aspects of the present invention provide for amplifying a plurality of markers in a single amplification reaction. Such an approach requires determining the proper reaction conditions (e.g., primer combinations, ionic strength, temperature conditions, etc.). Because some markers cannot be efficiently amplified, unambiguously identified after amplification, or are present in limiting amounts, more than one amplification reaction may be required. Thus, amplification of the markers comprises at least two multiplex amplification reactions in some embodiments. In some aspects, amplification of the markers comprises three multiplex amplification reactions. In some embodiments of the present invention in which the amplification of markers comprises three amplification reactions, the markers to be amplified in one multiplex amplification reaction comprise FGA and D9S747. In some embodiments, the markers to be amplified in one multiplex amplification reaction comprise D9162, MBP, IFN-A, and TH01, or any subcombination thereof. For example, one multiplex amplification reaction may include only D9162 and MBP. In some embodiments, the markers to be amplified in one multiplex amplification reaction comprise D21S1245 and D20S48.

While multiplex amplification reactions may be an efficient mechanism to detect LOH or MSI of a marker, each marker may be amplified individually. The individual amplification reaction products may then be combined prior analysis for LOH or MSI. Each amplification product may also be analyzed individually to determine if LOH or MSI is present.

Table 1 lists attributes of three multiplex reactions (MP1, MP2, and MP3) including the marker name; the chromosome (Chr) upon which each marker resides; the short tandem repeat sequence for each marker; the forward and reverse primers; and the dyes conjugated to the forward primer. For example, the STR for marker D4S243 is (ATAG)$_n$, where "ATAG" is the repeat unit and "n" is the number of times the unit is repeated. D4S243 is located on chromosome 4, and the forward primer is labeled with 6-FAM.

TABLE 1

| Multi-Plex | Marker | Chr. | STR | Forward Primer Sequence (5'-3') | Reverse Primer Sequence (5'-3') |
|---|---|---|---|---|---|
| MP1 | D4S243 | 4 | (ATAG)n | 6FAM-TCAGTCTCTCTTTCTCCTTGCA (SEQ ID NO: 1) | TAGGAGCCTGTGGTCCTGTT (SEQ ID NO: 2) |
| | FGA | 4 | (TTTC)n | VIC-GACATCTTAACTGGCATTCATG G (SEQ ID NO: 3) | CTTCTCAGATCCTCTGACACTCG (SEQ ID NO: 4) |
| | D9S747 | 9 | (GATA)n | VIC-GCCATTATTGACTCTGGAAAAG AC (SEQ ID NO: 5) | CAGGCTCTCAAAATATGAACAAAAT (SEQ ID NO: 6) |
| | D17S654 | 17 | (CA)n | NED-ACCTAGGCCATGTTCACAGC (SEQ ID NO: 7) | GAGCAGAATGAGAGGCCAAG (SEQ ID NO: 8) |
| | D17S695 | 16 | (AAAG)n | PET-CTGGGCAACAAGAGCAAAAT (SEQ ID NO: 9) | TTTGTTGTTGTTCATTGACTTCAGTC (SEQ ID NO: 10) |
| MP2 | D9S162 | 9 | (CA)n | NED-GCAACCATTTATGTGGTTAGGG (SEQ ID NO: 11) | TCCCACAACAAATCTCCTCAC (SEQ ID NO: 12) |

TABLE 1-continued

| Multi-Plex | Marker | Chr. | STR | Forward Primer Sequence (5'-3') | Reverse Primer Sequence (5'-3') |
|---|---|---|---|---|---|
| | MBP | 18 | (ATGG)n | 6FAM-GGACCTCGTGAATTACAATCACT (SEQ ID NO: 13) | ATCCATTTACCTACCTGTTCATCC (SEQ ID NO: 14) |
| | D16S310 | 16 | (ATAG)n | VIC-GGGCAACAAGGAGAGACTCT (SEQ ID NO: 15) | AAAAAAGGACCTGCCTTTATCC (SEQ ID NO: 16) |
| | THO1 | 11 | (TCAT)n | NED-AGGCTCTAGCAGCAGCTCAT (SEQ ID NO: 17) | TGTACACAGGGCTTCCGAGT (SEQ ID NO: 18) |
| | IFN-A | 9 | (GT)n | PET-TGCGCGTTAAGTTAATTGGTT (SEQ ID NO: 19) | GTAAGGTGGAAACCCCCACT (SEQ ID NO: 20) |
| MP3 | D21S1245 | 21 | (AAAG)n | VIC-CCAGAAAATGACACATGAAGGA (SEQ ID NO: 21) | TTGTTGAGGATTTTTGCATCA (SEQ ID NO: 22) |
| | D20S48 | 20 | (GT)n | NED-ATGGTCTCCAGTCCCATCTG (SEQ ID NO: 23) | TTGACCTGGATGAGCATGTG (SEQ ID NO: 24) |
| | D9S171 | 9 | (CA)n | NED-TCTGTCTGCTGCCTCCTACA (SEQ ID NO: 25) | GATCCTATTTTTCTTGGGGCTA (SEQ ID NO: 26) |
| | D16S476 | 16 | (AAAG)n | 6FAM-GGCAACAAGAGCAAAACTCC (SEQ ID NO: 27) | GGTGCTCTCTGCCCTATCTG (SEQ ID NO: 28) |

Amplified nucleic acids can be labeled in the present invention to help discriminate one amplified product from another. In some aspects of the present invention, one of the primers of the pair is labeled with a fluorescent dye. Table 1 identifies the fluorescent dyes ("6FAM," "VIC," "NED," and "PET") attached to the 5' end of the forward primers. The dyes' excitation maxima are distinct (520 nm, 554 nm, 575 nm, and 595 nm, respectively), which allows discrimination between similarly sized amplification products. A fluorescent dye, once attached to and oligonucleotide often exhibits a shift in its excitation maximum; but any excitation maximum referenced will the manufacturer's recited excitation maximum for the unconjugated dye. Other fluorescent dyes, capable of being attached to a nucleic acid primer, are contemplated in the present invention. In some aspects, at least two of the fluorescent dyes used to label the primers have different maximum fluorescent emission wavelengths.

When fluorescently labeled primers are used to amplify microsatellite markers, one aspect of the invention is using genetic analysis device capable of detecting emitted fluorescence. In some aspects, the genetic analysis device employs capillary electrophoresis to separate the amplification products and a CCD camera to detect emitted fluorescence from the products. For example, an ABI 3130 genetic analyzer utilizes capillary electrophoresis (CE) to separate amplification products by size. This device also has a laser light source to excite the fluorescent dyes and a CCD camera to detect the fluorescently labeled amplification products. The output from a CE device is often in the form of an electropherogram, which is a graphical representation of the light detected during electrophoresis, thus allowing an observer to quickly identify the presence, absence, or variation in an expected peak.

FIG. 1 depicts an electropherogram of the IFN-A locus. The top electropherogram is generated from a labeled amplification product originating from a buccal swab, while the bottom electropherogram is generated from a labeled amplification product originating from a urine sample. The buccal sample and the urine sample are from the same subject, which allows determination of acquired LOH or MSI in the bladder sample. For example, the electropherograms in FIG. 1 show LOH in the bladder sample. The last major peak in the buccal sample is approximately the same size as the previous peak. These two peaks represent two alleles of the microsatellite locus. In the bladder sample electropherogram of FIG. 1, there is only one major peak, indicating LOH at that locus.

Software is also available that identifies STR alleles by using defined signal collection bins. A "bin" corresponds to a particular region where amplification products are expected to be detected. The bin in FIG. 1 is illustrated as a thin rectangle above the electropherogram and indicates that the expected amplification products will be between 132 and 152 base pair range. The IFN-A alleles are the major peaks in the bin. However, for some microsatellites, alleles can be detected outside the assigned bin. For example, a homozygous allele in the D9S171 microsatellite is detected outside the D9S171 bin in the bottom electropherogram in FIG. 2.

Figure 3:
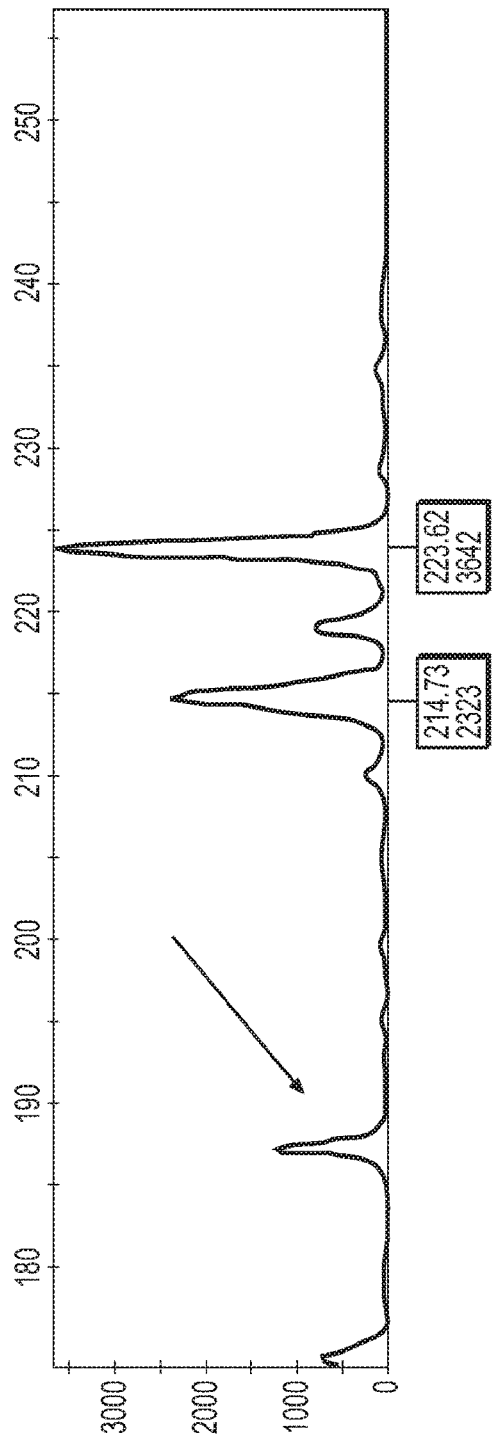
FIG. 3 illustrates an artifact detected in the D16S476 locus.
Figure 3:
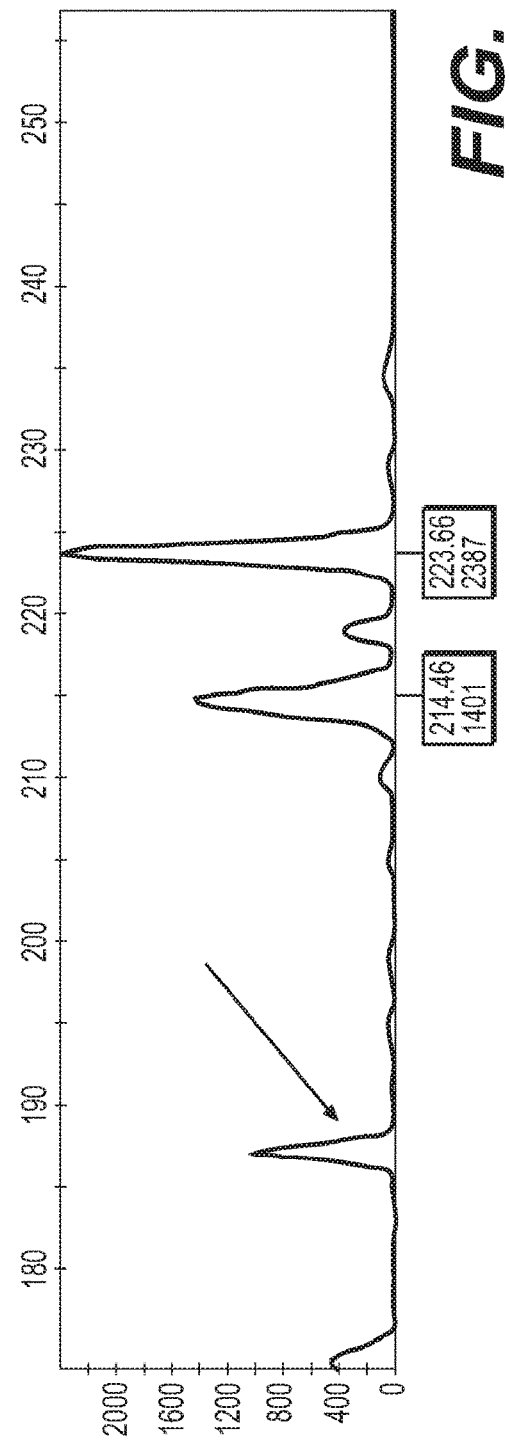

FIG. 3 illustrates the presence of artifacts in the amplified product. This artifact is a minor peak outside the bin for the D16S476 locus. When analyzing samples for MSI or LOH in the D16S476 locus, this artifact will not be considered as a separate allele. Artifacts of an amplification reaction will most often be present in the amplification products for the bladder and the buccal swab samples. As shown in FIG. 3, the artifact is constant in both samples.

EXAMPLES

The following examples are provided to further describe some of the embodiments disclosed herein. The examples are intended to illustrate, not to limit, the disclosed embodiments.

Example 1: Buccal Swab Extraction and Genomic DNA Extraction

Reagent preparation and buccal swab processing
a) Preparation Steps
Genomic DNA from buccal swabs was extracted using a commercially available protocol.
b) Methods for Avoiding Sample Cross-Contamination and Transferring of Swab to Microfuge Tube
To reduce or eliminate the possibility of cross-sample contamination, only one tube was opened at a time when adding wash reagents and gloves were changed if they came into contact with any sample liquid. Buccal swabs were placed into appropriately labeled 1.5 ml microcentrifuge tubes, and the lids were closed onto the base of the tips where the shaft meets the tip. The shafts were broken off and discarded into a biohazard waste container, and the microfuge tube was closed. Swab shafts were cut off with scissors when necessary, but in those cases, the scissors were decontaminated with 10% NaClO (bleach) between samples.
c) DNA Extraction from Buccal Swab
400 µl of Phosphate-buffered saline (PBS) solution was added to each sample tube. The tubes were vortexed vigorously for 50 seconds to assure that the swabs were completely saturated. Tubes were inverted 10 times to make sure PBS touched all areas of the tube. 20 µl of Qiagen Proteinase K stock solution and 400 µl of Buffer AL were added to each sample tube, and the tubes were inverted 75 times. The samples were vortexed thoroughly for 50 seconds to assure proper lysis and incubated at 56° C. for 60 minutes. The tubes were briefly centrifuged to remove condensation.

400 µl of 100% ethanol was added to each sample, and the tubes were inverted 50 times or for 1 minute and then vortexed vigorously for 50 seconds. The tubes were briefly centrifuged to remove condensation.

700 µl of lysate with ethanol were applied to the corresponding QIAamp spin columns without wetting the rim, and the lids were closed. Touching the QIAamp membrane with the pipet tip was avoided. The tubes were centrifuged at 8000 rpm for 1 minute, and the tubes containing the filtrate were discarded. The QIAamp spin columns were placed into clean 2 ml collection tubes. The nylon swabs were removed from the 1.5 ml tubes and placed into the appropriate labeled spin columns. When extracting DNA from the cotton swabs, the swabs were rubbed perpendicularly to the rim of the column to loosen the cotton fibers from the wood so that the swabs could be removed from the sticks and left in the columns. The tubes were centrifuged at 6000×g (8000 rpm) for 1 min, and the tubes containing the filtrate were discarded.

500 µl of Buffer AW1 was added to each column without wetting the rim. The lids were closed, and the tubes were incubated at room temperature for 5 minutes. The tubes were centrifuged at 8000 rpm for 1 minute, and the tubes containing the filtrate were discarded. The QIAamp spin columns were placed into clean 2 ml collection tubes.

500 µl of Buffer AW2 was added to each column without wetting the rim. The lids were closed, and the tubes were centrifuged at 14000 rpm for 3 minutes. The nylon/cotton swabs were removed from the columns. The QIAamp spin columns were placed into new collection tubes and centrifuged at 14000 rpm for 3 minutes. The tubes containing the filtrate were discarded.

The QIAamp spin columns were placed into clean, labeled 1.5 ml collection tubes, and the samples were incubated at 60° C. for 20-25 minutes with the lids open. 50 µl of Buffer AE (pre-warmed to 65° C.) was added to each column, and the samples were incubated at room temperature for 5 minutes. The tubes were centrifuged at 8000 rpm to elute the DNA from the columns, and the samples were stored at 4° C.

Example 2: Bladder Sample DNA Extraction a) DNA Extraction from Urine Sample
Bladder samples were obtained by collecting urine from the control and test subjects. Urine samples were equilibrated to room temperature (15-25° C.). Samples were swirled, and a Hemastix strip was quickly dipped in the urine to test for the presence of blood. The results of the Hemastix test were read after one minute and recorded.

Urine samples were transferred to a labeled 50 mL conical tube and centrifuged at 3500 rpm for 2 minutes. The supernatant was removed, and the length of the pellet was measured from the base of the conical tube. If the pellet measured less than 2 mm in length from the base of the conical tube, 250 µL of DNA-grade water was added to suspend the pellet. If the pellet measured more than 2 mm in length, 1 ml of DNA-grade water was added to suspend the pellet.

The samples were vortexed, and 250 µL of each sample was aliquoted to a 1.5 mL microcentrifuge tube. If there was more than 250 µL of sample, the extra sample was stored at −18±2° C. The total volume of urine and of water used to suspend the pellet was recorded, and the aliquot samples were stored at −18±2° C. until they were ready for extraction.

Samples were thawed at room temperature, and 1120 µL Buffer AVL/Carrier RNA was added to each 250 µL aliquot. The samples were vortexed for 15 seconds and incubated at room temperature (15-25° C.) for 10 minutes.

Each sample aliquot was split into 2 microcentrifuge tubes (685 µL each), and 560 µL of 96-100% ethanol was added to each tube. Tubes were vortexed for 15 seconds to remove drops from inside the lid.

622 µL of the solution from the first microcentrifuge tube of each sample was applied to the corresponding QIAamp spin column, the tubes were centrifuged at >8000 rpm for 1 minute, and the filtrates were discarded. The remaining 623 µL from the first microcentrifuge tube of each sample was added to the corresponding column, the tubes were centrifuged at >8000 rpm for 1 minute, and the filtrates were discarded. 622 µL of the solution from the second microcentrifuge tube of each sample was applied to the corresponding QIAamp spin column, the tubes were centrifuged at >8000 rpm for 1 minute, and the filtrates were discarded. The remaining 623 µL from the second microcentrifuge tube of each sample was added to the same column, the tubes were centrifuged at >8000 rpm for 1 minute, and the filtrates were discarded.

500 µL Buffer AW1 was added to the spin columns, the tubes were centrifuged at >8000 rpm for 1 minute, and the filtrates were discarded.

500 µL Buffer AW2 was added to the spin columns, the tubes were centrifuged at full speed (≥14000 rpm) for 3 minutes, and the filtrates were discarded. The tubes were centrifuged again at full speed for 1 minute.

QIAamp spin columns were placed in microcentrifuge tubes, and 30 μL pre-heated (70° C.) DNA-grade water were added to the columns. The samples were incubated at room temperature (15-25° C.) for 5 minutes. The tubes were centrifuged at >8000 rpm for 2 minutes to elute the DNA from the columns, the eluate was dried in a speed vac on low heat for 20 minutes of until the liquid had evaporated, and the DNA was dissolved in 30 μL of DNA-grade water. The DNA samples were stored at −18° C.±2° C. for short term storage (up to six months) or ≤−65° C. indefinitely. The work area was cleaned using 10% bleach, followed by deionized water.

b) Quantitation of Urine DNA

Quantifiler™ Human DNA Quantification Kits were used for the quantification of human genomic DNA. The kits are based on Taqman technology that uses two specific 5' nuclease assays. One is a target specific assay for total human DNA or for the Y chromosome (male), and the second is an internal PCR control (IPC), which detects inhibition due to too much DNA or common PCR inhibitors. The IPC components consist of an IPC template DNA, a synthetic sequence not found in nature, two primers, and one VIC-labeled probe. The target-specific assay components consist of two primers to amplify the target DNA and a Taqman MGB probe. This contains the 6-carboxyfluorescein (FAM) reporter dye coupled to the 5' end and a minor groove binder (MGB) with a nonfluorescent quencher (NFQ) coupled to the 3' end. The MGB increases the melting temperature of the probe without increasing its length. The Quantifiler™ Human DNA Quantification primers and probe target the human telomerase reverse transcriptase gene (hTERT) located at chromosomal position 5p15.33; the amplicon length is 62 bases. The Quantifiler-Y™ quantification primers target the sex-determining region of the Y gene (SRY) at chromosomal position Yp11.3; the amplicon length is 64 bases. During PCR, the TaqMan probe anneals to a specific region between the forward and reverse primers. When the probe is intact, the quencher is close enough to the reporter molecule to suppress reporter fluorescence. As the DNA-Polymerase extends through the primer the reporter molecule is cleaved from the probe, causing increased fluorescence. The fluorescence increase is proportional to the amount of PCR product produced. For both total and Y-specific DNA, the Quantifiler™ assay is used to quantify unknown samples by interpolating their quantity from a standard curve. The assay can accurately quantify 63 pg to 100 ng of human DNA.

c) Preparation Steps

All racks, bench tops and equipment were decontaminated with 10% bleach and thoroughly dried. Instruments and pipettes were cleaned with 10% bleach, then water, then 100% methanol and dried thoroughly. It was ensured that all equipment meets the minimum standards for quality control, where appropriate. Any supplies or equipment taken from a post-amplification room to a pre-amplification room were sterilized with 10% bleach before removal and again in the pre-amplification room prior to use.

To minimize the possibility of cross contamination between test and matched control samples, reagents were never transferred from a post-amplification room to a pre-amplification room. No reagent aliquots were returned to the original stock container.

The Quantifiler™ Human DNA standards were prepared fresh daily and stored at 5° C.±3° C. The Stock solution of DNA supplied with Quantifiler™ Kit is 200 ng/μL. The following quantities were used for the creation of a standard curve: 50 ng/μL, 16.7 ng/μL, 5.56 ng/μL, 1.85 ng/μL, 0.620 ng/μL, 0.210 ng/μL, 0.068 ng/μL and 0.023 ng/μL.

The appropriate amount of sterile water and Quantifiler™ Human DNA standard was added to each tube, and the tubes were vortexed for 30 seconds to mix thoroughly.

A negative (no template) control was prepared with 2 μL sterile water in place of template DNA. The appropriate Primer Mix was removed from the freezer, thawed, vortexed to mix and briefly centrifuge. Quantifiler™ PCR Reaction Mix was removed from the refrigerator and pipetted up and down to mix.

The PCR Master Mix was prepared as follows:

| Reagent | 1× Rxn Vol | (*n) × Rxn Vol |
|---|---|---|
| Quantifiler ™ Human Primer Mix | 10.5 | (1.1 × n) × 10.5 μL |
| Quantifiler ™ PCR Reaction Mix | 12.5 | (1.1 × n) × 12.5 μL |
| Total Volume | 23 | (1.1 × n) × 23 μL |

(*n) total number of reaction wells and 1.1 is the 10% overage.

23 μL master mix was aliquoted into all the wells. After vortexing the samples, 2 μL of each standard curve sample was added into the appropriate test wells of the 96 well plate. After all the standard curve samples have been added, 2 μL of the negative (No Template Control-water) was added to the appropriate wells, and 2 μL of the unknown samples was added to the appropriate test wells. The plate was covered with an adhesive tape, vortexed, and tapped to remove bubbles. Alternatively, the sample plate was centrifuged at 3000-4000 rpm for 2 minutes to bring the contents to the bottom of the wells and to remove any bubbles. The plate was placed on the ABI Prism 7500 and 7500 Fast Real Time PCR Systems for analysis.

d) Real Time PCR Analysis

The quantity of DNA present in each sample was determined by comparing its signal intensity to the intensity of the standard curve produced by the human DNA standard controls and dividing that number by 2 to give the ng/μl result. The standard curve results were examined to evaluate the quality of the results from the quantification standard reactions.

The standard curve is a graph of the CT of quantification standard reactions plotted against the starting quantity of the standards. The software calculates the regression line by calculating the best fit with the quantification standard data points. The $R^2$ value is a measure of the closeness of fit between the standard curve regression line and the individual CT data points of quantification standard reactions. A value of 1.00 indicates a perfect fit between the regression line and the data points.

It was ensured that the $R^2$ value was >0.98. If the $R^2$ value was less than 0.98, the following were checked: 1) preparation of serial dilutions of quantification standards, 2) loading of reactions for quantification standards, and 3) failure of reactions containing quantification standards.

A slope close to −3.3 indicates optimal (100%) PCR amplification efficiency. The typical slop range for the Quantifier Human kit is −2.9 to −3.3, with an average of −3.1. If the standard curve did not comply with the guidelines, no more than two outlier data points could be eliminated by designating those wells as not in use. The wells in the plate document that corresponded to the outlier data points were removed and the plate was reanalyzed to incorporate the change. If the elimination of those data points did not improve the standard curve, the quantification was considered invalid and had to be repeated.

The positive control was ±10% of the actual concentration.

Example 3: Amplification of Microsatellite Loci a) Optimal DNA Amount Used for MSA The amount DNA extracted per urine sample dictated how the assay would be performed. Optimally, a complete run using two multiplex PCR reactions was attempted. A concentration as low as 0.5 ng/µl in 15 µL of water could be used for testing of all multiplexes, using half the nominal concentration of DNA in each multiplex.

In cases where the total extracted DNA was less than 8 ng, the following guidelines were used to proceed with the assay: if 2.00-3.99 ng DNA was available from the urine sample, 2 ng DNA was used in each of PCRs 1, 2 and 3; if 4.00-6.99 ng DNA was available from the urine sample, 3.5 ng DNA was used in each of PCRs 1, 2 and 3; if 7.00-8.99 ng DNA was available from the urine sample, 4 ng DNA was used in each of PCRs 1, 2 and 3.

The same amount of DNA was run for buccal sample analysis and urine sample analysis, regardless of whether there was more buccal DNA.

Patient paired buccal and urine DNA was PCR amplified simultaneously in the same experiment, on the same thermal cycler, and under the same conditions.

b) PCR for MSA: Primer Sequences

PCR Primer pairs for MSA assay are presented in Table 1. Three multiplexes (MP1, MP2, MP3) were designed to amplify fourteen targets.

c) PCR for MSA: PCR Primer Master Mixes

For each primer assay master mix, each primer was diluted to a final working concentration of 2 pmol. The loci amplified in PCR1 were D4S243, FGA, D9S747, D17S654 and D17S695. The loci amplified in PCR2 were D9S162, MBP, IFN-A, TH01 and D16S310. The loci amplified in PCR3 were D21S1245, D20S48, D9S171 and D16S476.

For repeat singleplex reactions, primers were diluted to 5 µM by combining 87.5 µL of DNA-grade water and 6.25 µL of forward and reverse primers.

Primer assay master mixes were prepared in 100 µL for each primer mix and were scaled up to create more aliquots.

For PCR1, 145 µL of PCR grade water was added to a microcentrifuge tube. 5 µL of Forward and Reverse primers for D9S747, D17S64, and D17S695 were added.

In separate microcentrifuge tubes, the Forward and Reverse primers for D4S243 were diluted 2-fold by adding 5 µL of primer to 5 µL of PCR grade water, and 5 µL of the diluted Forward and Reverse primers were added to the primer mix. 7.54 of Forward and Reverse primers for FGA were added to the primer mix, and the primer master mix was thoroughly mixed. Single use 30 µL aliquots of the primer assay master mix were made.

For PCR2, 150 µL of PCR grade water was added to a microcentrifuge tube. 5 µL of Forward and Reverse primers for D9S162, MBP, IFN-A were added. In separate microcentrifuge tubes, the Forward and Reverse primers for D16S310 and TH01 were diluted 2-fold by adding 5 µL of primer to 5 µL of PCR grade water, and 5 µL of the diluted Forward and Reverse primers were added to the primer mix, and the primer master mix was thoroughly mixed.

For PCR3, 150 µL of PCR grade water were added to a microcentrifuge tube. 5 µL of Forward and Reverse primers for D21S1245 and D20S48 were added. In separate microcentrifuge tubes, the Forward and Reverse primers for D9S171 and D16S476 were diluted 2-fold by adding 5 µL of primer to 5 µL of PCR grade water, and 5 µL of the diluted Forward and Reverse primers were added to the primer mix, and the primer master mix was thoroughly mixed.

d) PCR for MSA: PCR

Reagent volumes were multiplied by the number of samples plus positive and negative controls to calculate the volumes needed for the master mix. For every ten samples, 10% was added to account for volume lost in pipetting. Lot numbers were recorded on an MSA Amplification Worksheet. The following reagents were combined, in order, to create the reaction mixture for PCRs 1, 2 and 3: 12.5 µL 2× FastStart Taqman Probe Master, 1 µL Primer Master Mix (1, 2 or 3) and 7.5 µL water, for a total of 21 µL.

21 µL master mix were aliquoted into each well for PCR1 and PCR2. For control reactions, 4 µL (multiplex 1, 2, 3) of control DNA were added to the wells for the positive control and 4 (multiplex 1, 2, 3) of water were added to the wells for the negative control. For each patient sample reaction, 4 ng (4 µL) of DNA were added to PCR1, PCR2 and PCR3. For patient samples to be analyzed by singleplex PCR for repeat reactions, 1 ng (1 µL) of DNA was added to PCR1 and PCR2. PCR plates (or PCR tubes in 96 well PCR rack) were centrifuged briefly at 3000 rpm for about 1 minute to bring all contents to the bottom of the plate.

The PCR conditions were as follows: one cycle of 95° C. for 11 minutes, 32 cycles of 94° C. for 1 minute, 55° C. for 1 minute and 72° C. for 1 minute, one cycle of 60° C. for 45 minutes, and a final hold at 4° C. Samples were then stored at −4° C. for short term storage or at −18° C. for long term storage. The PCR set-up area was cleaned with 10% bleach, followed by wiping with water and turning on the UV lamp for 5 minutes.

Example 4: Human DNA Identification with the ABI 3130 Genetic Analyzer a) Sample Preparation of PCR Reaction for Genetic Analyzer Sample loading buffer containing formamide (8.7 µL) and LIZ (0.3 size standard (9.0 µL total per well) was prepared. All unused wells in the plate column were filled with 10 µL formamide/LIZ master mix, and all wells in the adjacent even-numbered columns were filled with 10 µL formamide. 1.3 µL of each PCR reaction was added to the appropriate well of the sample plate, and the plate was centrifuged briefly to bring the contents to bottom of each well and remove bubbles.

The samples were heated at 95° C. for 3 minutes on a heat block and then placed on ice, at −18±2° C., on a cold block, or on a thermo cycler block at 4° C. for 2 minutes. The plate was assembled for the run by inserting septa in the sample plate, insert the samples into the plate base, and clamping on the plate retainer.

The Buffer Reservoir in position 1 was filled with fresh 1× Genetic Analysis Buffer (1:10 dilution prepared from 10×3130 Buffer EDTA), and reservoir in positions 2-4 were filled with water.

The ABI 3130 Genetic Analyzers analyzes fragment data in sets of two columns descending for 16 wells per analytical folder. Patient paired buccal and urine samples were electrophoresed on the same run and in the same folder of 16 well analyses.

a) Setting Up the Software for Genetic Analyzer

The software developed according to the invention, called PY software, is based on ABI 3130 Genetic Analyzer. It is operated by opening GeneMapperID ver 3.2 or higher, entering user ID (gmid) and password, selecting "Panel Manager" under the "Tools" button, selecting "NEW kit"

under "File", selecting "Microsatellite" and naming the panel "PY Test Panel", clicking OK, placing the arrow on the new kit named "PY Test Kit", selecting "New Panel" under "File", selecting "New Bins" under "Bins", naming the new Binset, selecting "New Panel" under "File", renaming Panel "Multiplex 1", selecting Multiplex 1, and entering the information for each marker in the chart. The same steps were repeated for Multiplex 2 and Multiplex 3.

To create the Analysis Method, Genemapper manager is selected under "Tools", the Analysis method editor is selected, and NEW is then selected, the new Analysis Method is named "PY SOP" on the General tab, and "PY Test" is selected under Binset on the Allele tab. The Ranger Filer button is selected, and the red channel is set to remove labels from 186.5 to 188. The Peak Detector, Peak Quality, and Quality tabs are set.

The size standard is set by selecting Gene mapper manager under Tools, selecting the Size Standard Tab, selecting GS500LIZ standard and open. The values in the standard should be entered and saved as 100, 139, 150, 160, 200, 300, 340, 350, 400, 450, 490, 500.

The instrument Protocol For 3130 analyzer is set by opening 3130 Data collection software, selecting "Module Manager" and selecting "New", selecting "FragmentAnalysis36_POP4:" as the template, creating a new name for Module, such as FragmentAnalysis36_POP4_1.

The run settings are set as follows: Oven temperature 60° C., Pre run voltage 15, Pre run time 180 seconds, Injection voltage 3.1 Kvolt, Injection time 8 second (or 5 seconds for re-injection of samples), Voltage number of steps 10NK, Voltage step interval 60 seconds, Data delay time 1 second, Run voltage 15 volts, Run time 1500 sec.

Protocol Manager is selected, and "New" is selected, a name for the protocol is created, such as "New Test Protocol", the Type is selected as "Regular", the Run module is set to the module created above for the 3130 analyzer, and the Dyeset is set to G5.

To prepare the Sample sheet, Applied Biosystems—Data Collection—Run Data Collector 2.0 is selected, the GA3130 folder is opened, "Plate Manager" is selected, option is selected, "New" is selected, and the name of the Plate is entered and recorded on the MSA PCR amplification worksheet. "GeneMapper-(Name of Computer)" is selected from Application and Owner name and Operator Name are filled in. On the GeneMapper plate editor screen, the sample name is entered, priority is set to 100, sample type is selected, size standard is set to Test Standard settings, either test panel/multiplex 1 (PCR 1) or multiplex 2 (PCR 2) is selected, depending on which multiplex is run, analysis method is set to "choose new test," sections titled SNP are skipped, set user define 1, 2, and 3, Results group 1 is set to STR, Instrument protocol 1 is set to TEST PROTOCOL.

To perform the run, the folder entitled "3130" is opened, Run Scheduler is selected, "Find All" is selected, the run of interest is selected, the desired plate is highlighted, and the run is started. It took approximately 45 minutes to run 2 lanes, and when the runs were complete, the plates were removed, sealed with a Costar Thermowell sealer, and stored at −18±2° C. for up to 1 week.

4-C: Analyzing MSA Data with PY Software

The data was imported to GeneMapperID ver 3.2 or higher and analyzed by the program. Manual editing of samples was carried out as necessary. To manually edit a sample whose SQ column has a red or yellow flag, size match editor (designated by size standard peaks) was selected, and the sizes of the peaks that were incorrect were manually changed by pressing "Override SQ" and "Apply", and the samples were then re-analyzed.

c) Determining MSA Peak Sizes

Figure 2:
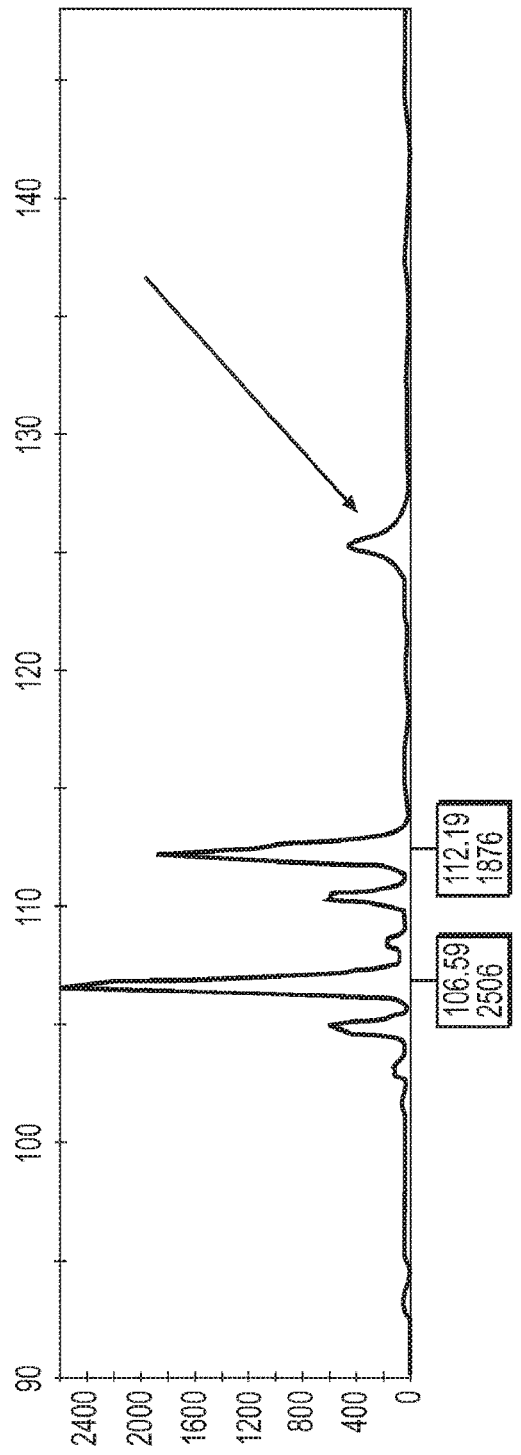
FIG. 2 illustrates the detection of addional alleles in the D9S171 locus.
Figure 2:
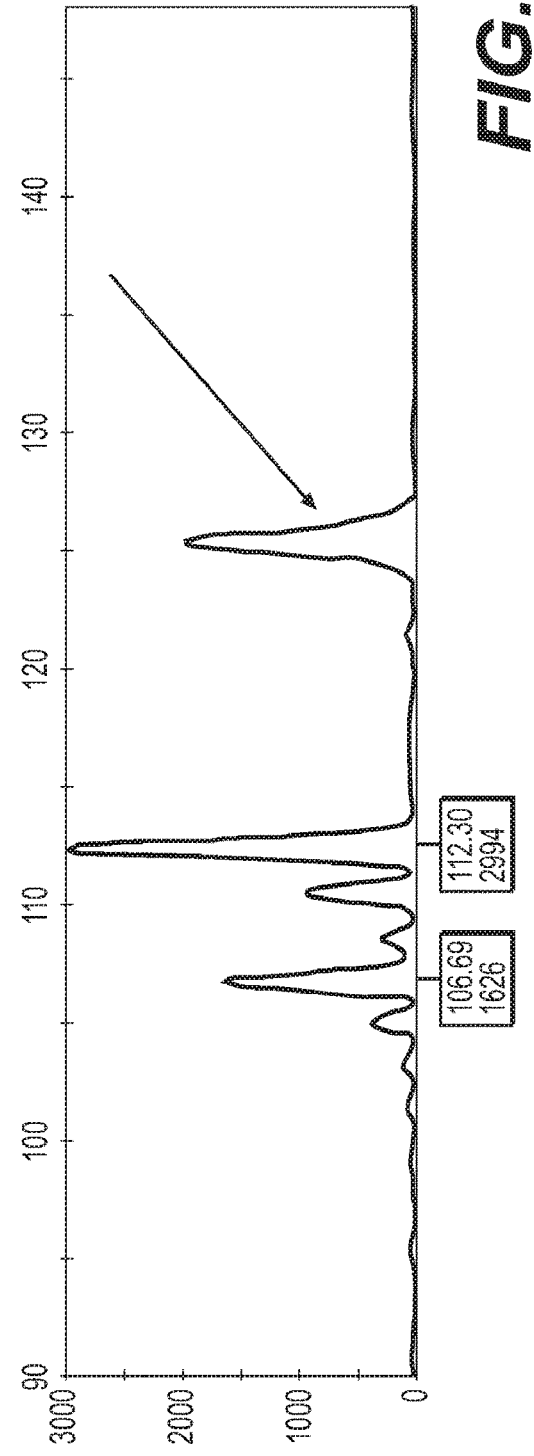

Each analysis included data for paired patient samples of buccal DNA and urine DNA. These were viewed together. (i.e. 2 samples for PCR1, 2 samples for PCR2 and 2 samples for PCR3). The 2 samples to be sized were highlighted, and "Display Plots" was selected. The plots were reviewed by comparing the buccal sample to the urine sample for each multiplex reaction. Each channel (blue, red, yellow, green) was reviewed for each sample and each multiplex. Allele-specific considerations for assigning peaks was done. Examples of the patterns for IFN-α, D9S171 and D16S476 are shown in FIGS. 1-3. Upon completion of sizing, the Genotype Tab is selected, and "MSA ANALYSIS format is selected, and the genotype information is used for statistical interpretation for acceptance criteria.

d) Interpretation of Fragment Size Analysis on 3130 Genetic Analyzer

The analysis for each sample was performed by one analyst, and the data entry was verified by a second analyst. The GeneMapper peak size and height data table was accessed, and Acceptance Criteria was established using more than 40 surgically resected bladder cancer samples and their controls and are shown in Table 2.

TABLE 2

MSA Markers Analyzed

| Locus: | Repeat Type: | Size Range: | Color Channel: | K562~allele sizes: |
|---|---|---|---|---|
| D4S243 | (ATAG)n | 165-192 bp | Blue | 169 bp |
| FGA | (TTTC)n | 299-361 bp | Green | 328 bp |
| D9S747 | (GATA)n | 179-201 bp | Green | 185 bp |
| D17S654 | (CA)n | 194-218 bp | Yellow | 216 bp |
| D9S162 | (CA)n | 117-148 bp | Yellow | 143 bp |
| D17S695 | (AAAG)n | 170-220 bp | Red | 185, 200 bp |
| MBP &A | (ATGG)n | 200-242/119-151 | Blue | 207, 215, 119 bp |
| D21S1245 | (AAAG)n | 209-293 bp | Green | 236, 255 bp |
| D16S310 | (ATAG)n | 127-170 bp | Green | 155, 160 bp |
| D20S48 | (GT)n | 251-269 bp | Yellow | 261 bp |
| THO1 | (TCAT)n | 174-209 bp | Yellow | 198 bp |
| D9S171 | (CA)n | 109-129 bp | Yellow | 126 bp |
| D16S476 | (AAAG)n | 176-230 bp | Red | 187 209 bp |
| IFN-A | (GT)n | 132-152 bp | Red | no product |

For samples to be called "normal", the amplification products had to match the sizes (±1 bp) and colors indicated in Table 2 and have a minimum of 100 relative fluorescent units (RFU) for each heterozygous allele and a minimum of 200 RFU for homozygous alleles. The negative control did not produce PCR products for any loci (RFU <100).

For samples to be called "cancer", the amplification products had to match the sizes (±1 bp) and colors indicated in Table 2. For buccal samples to be called "cancer", the amplification products had to have a minimum of 100 relative fluorescent units (RFU) for each heterozygous allele and a minimum of 200 RFU for homozygous alleles. For urine samples to be called "cancer", the amplification products had to have a minimum of 100 relative fluorescent units (RFU) for at least one allele, and for two peaks to be considered alleles, the RFUs had to be within 40% of one another. The maximum RFUs for an allele was 5000 RFU. The cutoff values for each of the markers for determining LOH, based on published data and the analysis done here, are shown in Table 3.

TABLE 3

Cutoff Values by Marker (outside of range = LOH)

| Marker | Lower Limit | Upper Limit |
| --- | --- | --- |
| D4S243 | 0.68 | 1.33 |
| FGA | 0.60 | 1.43 |
| D9S747 | 0.63 | 1.42 |
| D17S654 | 0.71 | 1.36 |
| D17S695 | 0.49 | 1.61 |
| MBP | 0.63 | 1.45 |
| MBPA | 0.71 | 1.37 |
| D16S310 | 0.6 | 1.34 |
| D9S162 | 0.51 | 1.53 |
| THO1 | 0.46 | 1.53 |
| IFN-A | 0.68 | 1.43 |
| D21S1245 | 0.58 | 1.42 |
| D20S48 | 0.62 | 1.46 |
| D9S171 | 0.72 | 1.36 |
| D16S476 | 0.54 | 1.65 | e) Data Analysis from Buccal Swab Based MSA

Sample data were in ordered pairs for analysis. The descending order by sample was as follows: Buccal 1 with results for each locus in multiplex 1, Urine 1 with results for each locus in multiplex 1, Buccal 1 with results for each locus in multiplex 2, Urine 1 with results for each locus in multiplex 2, Buccal 3 with results for each locus in multiplex 3, Urine 3 with results for each locus in multiplex 3. HL60 data were organized as follows: Multiplex 1, Multiplex 2 and Multiplex 3. Loci were listed in the same order as those for the buccal. Column headings of the spreadsheet were as follows: Sample ID, locus, allele 1 size, allele 2 size, two empty columns, allele 1 peak height, allele 2 peak height. Data were imported into Excel for analysis.

The data was compared to the acceptance criteria above to determine whether the data passed or failed the acceptance criteria. If a sample failed the acceptance criteria, it was not used in the evaluation. To determine the status of a sample, the data was entered into the Excel Spreadsheet "MSA Sample spreadsheet.xls". This spreadsheet uses the following calculation to determine the ratio of buccal to urine peak height: Ratio=(urine 1 allele 1 peak height/urine 1 allele 2 peak height)/buccal 1 allele 1 peak height/buccal 1 allele 2 peak height. The ratio and Negative/Positive for MSI or LOH marker status were automatically determined using the calculations based on the acceptance criteria for each locus.

Loci demonstrating LOH (through loss of an allele) were considered positive for LOH, although ratios cannot be calculated for loci demonstrating complete loss. The ratio was only calculated for heterozygous loci and loci with complete data sets. The ratio was compared with the cutoff data. Ratios falling outside the cutoff ranges were considered positive for LOH. Ratios falling within the range were designated negative for MSI/LOH. If additional or shifted alleles were detected in the urine, the loci were determined to be positive for MSI if the additional or shifted alleles were shifted ±3 bp within the bins, and the additional or shifted alleles had a minimum peak height of 100 RFU.

f) Evaluation of Result from 3130 Genetic Analyzer: The Test Repeat Criteria

Repeat criteria were established for repeat testing when sufficient DNA remained to run the assay. If sufficient DNA was not present, the results from the original run were considered valid for all loci meeting the acceptance criteria for the assay and were reported. If an entire HL60 multiplex positive controls failed to meet the acceptance criteria, the sample data for the multiplex(es) that contained the failed loci were not evaluated, and the appropriate HL60 and sample multiplexes were repeated at the original DNA concentration. If one or more loci within an HL60 control multiplex failed to meet the acceptance criteria, the sample data for the loci corresponding to the failed was not evaluated. The appropriate HL60 and sample multiplexes were repeated at the original DNA concentration and only results for the loci that failed during the first run were reported in the MSA Sample Spreadsheet. Data from loci that passed the acceptance criteria during the first run were removed from the sample sheet in the second run. If an entire sample multiplex failed the acceptance criteria, the multiplex was repeated using the original concentration of DNA. If a sample had a single locus with positive result, that locus was repeated in singleplex using 1 ng of DNA and 5 µM of each primer, and the results from both tests were reported. Loci containing additional urine peaks that indicated microsatellite instability were repeated in singleplex to confirm the additional peak, as described above. If any alleles within a locus had a peak height >5000 (off scale), loci were re-evaluated by re-injection of the multiplex with an injection time of 5 seconds.

A decision flow chart was used to determine which loci to include in the re-injection evaluation. Homozygous alleles within a peak height >5000 were not re-injected if they did not interfere with the ability to evaluate other loci. If re-injection values were used, both the buccal and urine values from the re-injected samples were reported in lieu of the buccal and urine values for the off-scale or obscured peaks obtained in the first run. If still off scale or obscured, the result was Not Evaluable.

g) Final Reporting of Sample Results

Following all re-injection or repeat results, the final determination of each locus of a sample was reported on the original sample spreadsheet containing the multiplex data.

Example 5: Clinical Test—Detection of Bladder Cancer by MSA of Urinary Sediment a) Samples The PY SOP and PY Test were used to predict the presence or lack of bladder cancer in human biological samples. 5 matched buccal swabs and urine samples from "normal" patients and 5 matched buccal swabs and urine samples from bladder cancer patients were analyzed, along with positive and negative DNA sample controls and, a no template negative control. Each sample was identified with a unique specimen ID as assigned by the designated CLIA test lab (DCTL) sample accessioning group. All specimens were handled per CAP and CLIA regulations, insuring sample tracking throughout the testing process.

b) PCR for MSA

An MSA assay was carried out. The assay consisted of DNA extraction, normalization, and PCR amplification of STR markers of matched buccal swab and urine sediment genomic DNA. The PCR was done using primer sets that flank the target STRs at 14 microsatellite loci. The 5' end of each primer pair was fluorescently labeled to allow for detection of the PCR fragments by capillary electrophoresis. The primer pairs from Table 1, above, were used.

The PCR amplicons were resolved on a capillary-based gel electrophoresis system that detects, sizes and determines the relative fluorescence units (RFU) for each fragment.

Figure 4:
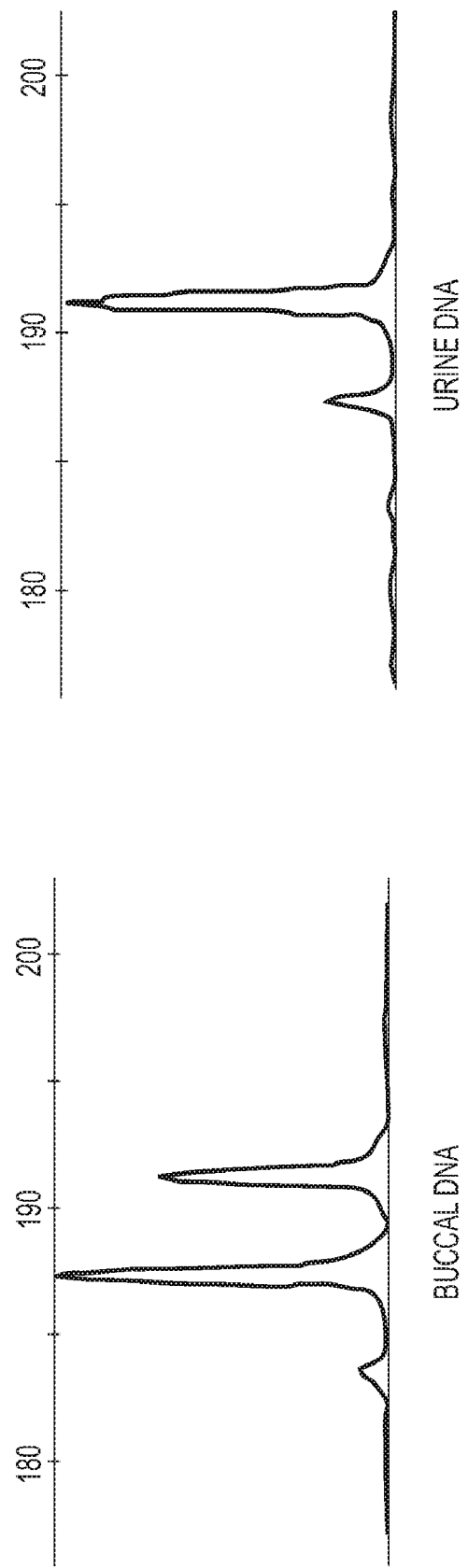
FIG. 4 provides an electropherogram of showing LOH at an STR marker located at 9q32.

The RFUs of heterozygous alleles detected in the buccal swab DNA were compared to the RFUs detected in the matched urine sample, and the ratio of RFUs from urine alleles to blood alleles was calculated. Markers that exhibited values outside the ratios seen in normal samples were said to exhibit a loss of heterozygosity (LOH) that served as an indicator of bladder cancer. See FIG. 4 for an example electropherogram.

c) MSA Assay Controls

Each sample and control was electrophoresed in the presence of a size standard that was used to calculate the fragment size of each PCR product. Positive Control Genomic DNA was from the American Tissue Culture collection (ATCC) and from Applied Biosystems. The controls were tested at a concentration at the lower limit of detection as determined in the clinical validation of the sample.

d) Instrument and Software

The instrument used for the assay was the 3130xl Genetic Analyzer from Applied Biosystems, a 16 capillary instrument capable of generating genotyping data in 1 hour. The 3130xl Genetic analyzer handles a wide variety of gene detection assays, including DNA sequencing, SNP genotyping, and fragment analysis. The 3130xl genetic analyzer operates using the Genemapper Software v2.0, which is 21 C.F.R. Part 11 compliant. In accordance with CAP regulations, the instrument was calibrated semi-annually with regard to spectral and spatial calibration.

e) Sample Collection and Preparation

Two specimen types were collected: a buccal swab and urine sediment. The buccal swab was collected by a designated CLIA test lab (DCTL) using a collection kit and following clearly defined collection instructions. Briefly, (1) The buccal swab is stable for one week at 4° C.; (2) once received at a DCTL, each case was accessioned and assigned a unique identifier that followed the sample through the entire extraction process; (3) genomic DNA was extracted from the sample in CAP-accredited laboratories. The human DNA in the sample was quantified using the Quantifiler real-time PCR kit from Applied Biosystems, and the genomic DNA was normalized to 1 ng/µl.

Urine sediment was collected by a DCTL using a collection kit and following clearly defined collection instructions. Briefly, (1) urine was collected in a sterile collection cup, and a preservative was added to stabilize the DNA in the urine. The urine and preservative were mixed, and the urine nucleic acids and proteins were preserved at room temperature for shipment. (2) Genomic DNA was purified form the urine sediment using the Urine DNA Isolation Maxi Kit from Norgen Biotech. This kit isolates both high molecular weight DNA (greater than 1 kb in size; mostly cell associated) and small molecular weight DNA (150-250 bp; derived from the circulation) from 25 mL to 80 mL of urine. The human DNA in the sample was quantified using the Quantifiler real-time PCR kit from Applied Biosystems, and the genomic DNA was normalized to 1 ng/µl.

A set of matching urine and buccal swab specimens were obtained from 5 patients diagnosed with bladder cancer and a set of matching sets from 5 normal-healthy patients. The samples were obtained from Bioreclaimation LLC. Two buccal swabs were collected from normal patients and one buccal swab was collected from cancer patients. Samples were de-identified, with any HIPPA sensitive information removed, by Bioreclaimation, and a sample ID was assigned by Bioreclaimation for each specimen.

Biometric data for each specimen is provided in FIG. 5, and the sample numbers are shown in Table 4.

TABLE 4

Sample numbers for analysis

5 Normal Swab and Urine Matches

| Urine Lot # : | 1st swab | 2nd swab |
|---|---|---|
| BRH769882 | BRH769887A | BRH769887B |
| BRH769883 | BRH769888A | BRH769888B |
| BRH769884 | BRH769889A | BRH769889B |
| BRH769885 | BRH769890A | BRH769890B |
| BRH769886 | BRH769891A | BRH769891B |

5 Cancer Swab and Urine Matches

| Urine Lot # : | Swab |
|---|---|
| BRH777321 | BRH777326 |
| BRH777322 | BRH777327 |
| BRH777323 | BRH777328 |
| BRH777324 | BRH777329 |
| BRH777325 | BRH777330 | f) DNA Extraction from Samples

The urine samples were centrifuged to pellet cells. The urine was decanted, and the pellets were resuspended in water. 250 µL of urine sediment slurry was pipetted into microtubes, and the remainder of the urine sediment was saved and stored at −20°±2° C. Buffer AVL/Carrier RNA was added to each sample. Samples were vortexed and incubated at room temperature for 10 minutes. The QIA amp Viral RNA Mini Kit instructions were followed for genomic DNA extraction.

g) DNA Quantitation and Normalization

Real Time PCR (TaqMan quantitative PCR) was used to determine the concentration of human DNA in an extracted sample by direct assay of 1 ng of DNA as determined by OD260 (see CBI DNASEQ00035). Human Beta Actin gene is the target of the Taqman assay. A standard curve of human DNA standard with a known concentration was used to compare results from the sample extract to determine concentration. TaqMan can determine even slight differences in concentration and is sensitive down to 10 copies of DNA molecules. Once the sample DNA concentration was determined, the sample was normalized to 1 ng/µl. The DNA concentrations in for the samples are shown in Table 5.

TABLE 5

DNA concentrations of patient samples

| Sample ID's | Test ID | State | Quants (ng/µL) | Elution Volume (µl) | Total Concentration (ng) |
|---|---|---|---|---|---|
| BRH769883 | PY MSA | Urine-Normal | 25.39 | 56.00 | 1421.84 |
| BRH769882 | PY MSA | Urine-Normal | 0.32 | 56.00 | 17.92 |
| BRH769885 | PY MSA | Urine-Normal | 7.00 | 56.00 | 392.00 |
| BRH769884 | PY MSA | Urine-Normal | 1.38 | 56.00 | 77.28 |
| BRH769886 | PY MSA | Urine-Normal | 5.55 | 56.00 | 310.80 |
| BRH769890A | PY MSA | Buccal-Normal | 0.40 | 46.00 | 18.40 |

TABLE 5-continued

DNA concentrations of patient samples

| Sample ID's | Test ID | State | Quants (ng/μL) | Elution Volume (μl) | Total Concentration (ng) |
|---|---|---|---|---|---|
| BRH769890B | PY MSA | Buccal-Normal | 1.71 | 46.00 | 78.66 |
| BRH769888A | PY MSA | Buccal-Normal | 3.81 | 46.00 | 175.26 |
| BRH769888B | PY MSA | Buccal-Normal | 6.32 | 46.00 | 290.72 |
| BRH769889A | PY MSA | Buccal-Normal | 15.14 | 46.00 | 696.44 |
| BRH769889B | PY MSA | Buccal-Normal | 9.98 | 46.00 | 459.08 |
| BRH769891A | PY MSA | Buccal-Normal | 0.33 | 46.00 | 15.18 |
| BRH769891B | PY MSA | Buccal-Normal | 4.13 | 46.00 | 189.98 |
| BRH769887A | PY MSA | Buccal-Normal | 11.98 | 46.00 | 551.08 |
| BRH769887B | PY MSA | Buccal-Normal | 13.89 | 46.00 | 638.94 |
| BRH777326 | PY MSA | Buccal-Cancer | 16.05 | 46.00 | 738.30 |
| BRH777327 | PY MSA | Buccal-Cancer | 10.96 | 46.00 | 504.16 |
| BRH777328 | PY MSA | Buccal-Cancer | 6.65 | 46.00 | 305.90 |
| BRH777329 | PY MSA | Buccal-Cancer | 4.91 | 46.00 | 225.86 |
| BRH777330 | PY MSA | Buccal-Cancer | 41.22 | 46.00 | 1896.12 |
| BRH777321 | PY MSA | Urine-Cancer | 1.00 | 56.00 | 56.00 |
| BRH777322 | PY MSA | Urine-Cancer | 26.57 | 56.00 | 1487.92 |
| BRH777323 | PY MSA | Urine-Cancer | 5.40 | 56.00 | 302.40 |
| BRH777324 | PY MSA | Urine-Cancer | 37.75 | 56.00 | 2114.00 |
| BRH777325 | PY MSA | Urine-Cancer | 279.21 | 56.00 | 15635.76 | h) MSA PCR and Analysis

The MSA PCRs were carried out as described in Example 3 using Amplitaq gold as the enzyme. The Acceptance Criteria described in Example 3 and shown in Table 2 were used. The analysis was carried out as described in Example 4, and the cutoff values presented in Table 3 were used to detect LOH and MSI. The criteria presented in Example 4f were used to classify LOH or MSI.

i) Results

Table 6 provides the Sample Pair IDs and their corresponding urine and buccal swab Sample IDs provided by Bioreclamation.

TABLE 6

Sample Pair IDs and corresponding Sample IDs from BioReclamation LLC

| Sample Pair ID | Bioreclamation ID Matched sets | | |
|---|---|---|---|
| Normal | Urine Lot #: | 1st swab | 2nd swab |
| N1 | BRH769882 | BRH769887A | BRH769887B |
| N2 | BRH769883 | BRH769888A | BRH769888B |
| N3 | BRH769884 | BRH769889A | BRH769889B |
| N4 | BRH769885 | BRH769890A | BRH769890B |
| N5 | BRH769886 | BRH769891A | BRH769891B |

5 Cancer Swab and Urine Matches

| Bladder Cancer | Urine Lot #: | Swab |
|---|---|---|
| C1 | BRH777321 | BRH777326 |
| C2 | BRH777322 | BRH777327 |
| C3 | BRH777323 | BRH777328 |
| C4 | BRH777324 | BRH777329 |
| C5 | BRH777325 | BRH777330 |

FIGS. 6a-6e, respectively show the raw MSA data for the Sample Pair IDs N1-N5 as defined in Table 6. FIGS. 6f-6j, respectively show the raw MSA data for the Sample Pair IDs C1-C5 as defined in Table 6.

Table 7 shows the results of the MSA carried out, with "N"=normal (no LOH), "LOH"=loss of heterozygosity between a paired buccal and urine sample, and "MSI"=microsatellite instability observed in a paired buccal and urine sample. "Final call" is considered "N" if fewer than two loci exhibited LOH or MSI, or "C" for cancerous if two or more loci exhibited LOH or MSI.

TABLE 7

Summary of MSA results

| | MSA results Buccal/Urine Pairs Sample Pair ID | | | | | | | | | |
|---|---|---|---|---|---|---|---|---|---|---|
| Loci | N1 | N2 | N3 | N4 | N5 | C1 | C2 | C3 | C4 | C5 |
| MSA D4-S243 | NI | N | N | N | N | N | N | N | NI | N |
| Panel FGA | N | N | N | N | N | N | N | N | LOH | N |
| D9-S747 | N | N | N | N | NI | N | NI | NI | LOH | M-SI |
| D17-S654 | N | N | N | NI | N | N | NI | N | N | N |
| D17-S695 | N | N | N | NE | NI | NI | N | NI | N | N |
| MBP | N | N | N | N | IN | LOH | N | LOH | NI | L-OH |
| MBPA | N | N | NI | N | N | N | NI | NI | N | N |
| D16-S310 | N | N | N | N | NI | NI | N | N | N | N |
| D9-S162 | NI | NI | N | NI | N | N | N | Ni | LOH | N |
| THO1 | NI | NI | N | N | N | N | N | LOH | LOH | N |
| IFN-A | NI | NI | N | N | N | N | N | LOH | N | NI |
| D21-S1245 | NI | N | NE | N | N | N | MSI | NI | LOH | L-OH |
| D20-S48 | N | N | NI | N | N | LOH | LOH | N | N | N |
| D9-S171 | N | N | N | N | NI | N | NI | NI | N | N |
| D16-S476 | NI | N | N | N | N | N | NI | NI | NI | N |
| Final Call | N | N | N | N | N | C | C | C | C | C |

NI = NON-INFORMATIVE (HOMOZYGOUS)
NE = NON-EVALUABLE (AMPLIFICATION FAILED)
LOH = LOSS OF HETEROZYGOSITY
N = Normal
MSI = microsattelite instablity
C = Cancer In summary, samples clinically diagnosed and confirmed by cystoscopy were determined to positive for the disease by the MSA methods presented here. Each of the normal controls were negative for MSI and LOH for all of the 14 markers tested. For the bladder cancer samples, at least two of eight particular markers were positive for LOH. The eight markers were FGA, D98747, MBP, D98162, TH01, IFN-A, D21S1245 and D20S48. Therefore, the buccal-based MSA analysis presented here requires the use of only eight markers to accurately detect bladder cancer.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the The disclosures of each patent, patent application, and publication cited or described in this document are hereby incorporated herein by reference, in its entirety.

What is claimed:

1. A method for analyzing heterozygosity in microsatellite loci from a bladder sample and a matched control buccal sample from a human subject, the method comprising:
   a) using a plurality of pairs of primers to amplify a set of microsatellite markers from the bladder sample and the buccal matched control sample to produce a set of amplification products, wherein the set of microsatellite markers comprises FGA, D9S747, MBP, D9S162, THO1, IFN-A, D21S1245, and D20S48, and wherein at least one of the primers of each pair of primers is labeled with a fluorescent dye to provide relative fluorescent units of each amplification product; and,
   b) calculating ratios of RFUs of each amplification product from the bladder sample to RFUs of each amplification product from the buccal matched control sample, wherein a calculated ratio falling outside a cutoff range of a ratio of an amplification product from a normal bladder sample to an amplification product from a buccal matched control indicates loss of heterozygosity (LOH) in the microsatellite locus, wherein:
   (1) a primer consisting of SEQ ID NO: 3 and an optional fluorescent dye label and (2) a primer consisting of SEQ ID NO: 4 and an optional fluorescent dye label are the pair of primers for FGA;
   (3) a primer consisting of SEQ ID NO: 5 and an optional fluorescent dye label and (4) a primer consisting of SEQ ID NO: 6 and an optional fluorescent dye label are the pair of primers for D9S747;
   (5) a primer consisting of SEQ ID NO: 13 and an optional fluorescent dye label and (6) a primer consisting of SEQ ID NO: 14 and an optional fluorescent dye label are the pair of primers for MBP;
   (7) a primer consisting of SEQ ID NO: 11 and an optional fluorescent dye label and (8) a primer consisting of SEQ ID NO: 12 and an optional fluorescent dye label are the pair of primers for D9S162;
   (9) a primer consisting of SEQ ID NO: 17 and an optional fluorescent dye label and (10) a primer consisting of SEQ ID NO: 18 and an optional fluorescent dye label are the pair of primers for THO1;
   (11) a primer consisting of SEQ ID NO: 19 and an optional fluorescent dye label and (12) a primer consisting of SEQ ID NO: 20 and an optional fluorescent dye label are the pair of primers for IFN-A;
   (13) a primer consisting of SEQ ID NO: 21 and an optional fluorescent dye label and (14) a primer consisting of SEQ ID NO: 22 and an optional fluorescent dye label are the pair of primers for D21S1245; and/or
   (15) a primer consisting of SEQ ID NO: 23 and an optional fluorescent dye label and (16) a primer consisting of SEQ ID NO: 24 and an optional fluorescent dye label are the pair of primers for D20S48.

2. The method of claim 1, wherein amplification of the set of microsatellite markers comprises at least two multiplex amplification reactions.

3. The method of claim 2, wherein the amplification of the set of microsatellite markers comprises three multiplex amplification reactions, and wherein each multiplex amplification reaction comprises a different combination of markers from the set of microsatellite markers.

4. The method of claim 3, wherein templates for the first multiplex reaction amplification comprise markers FGA and D9S747.

5. The method of claim 3, wherein templates for the second multiplex reaction amplification comprise markers D9S162, MBP, IFN-A, and THO1.

6. The method of claim 3, wherein templates for the third multiplex reaction amplification comprise markers D21S1245 and D20S48.

7. The method of claim 1, wherein at least two of the fluorescent dyes used to label the primers have different maximum fluorescent emission wavelengths.

8. The method of claim 1, wherein the bladder sample is obtained from a urine sample, or is a bladder biopsy sample.

9. The method of claim 1, wherein the bladder sample is a bladder biopsy sample.

10. The method of claim 1, wherein the matched control buccal sample is buccal cells.

11. The method of claim 1, wherein the set of microsatellite markers further comprises D4S243, D17S654, D17S695, D16S310, D9S171, and D16S476.

12. The method of claim 11, wherein the amplification of the set of markers comprises three multiplex amplification reactions, and wherein each multiplex amplification reaction comprises a different combination of markers from the set of microsatellite markers.

13. The method of claim 12, wherein a first multiplex reaction amplifies markers D4S243, FGA, D9S747, D17S654, and D17S695.

14. The method of claim 12, wherein a second multiplex reaction amplifies markers D9162, MBP, IFN-A, THO1, and D16S310.

15. The method of claim 12, wherein a third multiplex reaction amplifies markers D21S1245, D20S48, D9S171, and D16S476.

16. The method of claim 1, wherein the upper and lower limits of the cutoff ranges of the ratios of the RFU of each amplification product from the normal bladder sample to the RFU of each amplification product from the buccal matched control sample are as follows:

| Marker | Lower Limit | Upper Limit |
| --- | --- | --- |
| FGA | 0.60 | 1.43 |
| D9S747 | 0.63 | 1.42 |
| MBP | 0.63 | 1.45 |
| D9S162 | 0.51 | 1.53 |
| THO1 | 0.46 | 1.53 |
| IFN-A | 0.68 | 1.43 |
| D21S1245 | 0.58 | 1.42 |
| D20S48 | 0.62 | 1.46. |

17. The method of claim 1, wherein the primers consisting of SEQ ID NO: 3, 5, 11, 13, 17, 19, 21, and 23 are labeled with a fluorescent dye.

18. The method of claim 17, wherein the fluorescent dye is VIC, NED, 6FAM, or PET.

19. The method of claim 17, wherein the fluorescent dye is attached to the 5' end of the primer.

20. The method of claim 18, wherein:
the 5' end of the primers consisting of SEQ ID NO: 3, 5, and 21 are labelled with VIC;
the 5' end of the primers consisting of SEQ ID NO: 11, 17, 23 are labelled with NED;
the 5' end of the primer consisting of SEQ ID NO: 13 is labelled with 6-FAM; and/or
the 5' end of the primer consisting of SEQ ID NO: 19 is labelled with PET.

21. The method of claim 1, wherein:
a primer consisting of SEQ ID NO: 3 and a fluorescent dye label and a primer consisting of SEQ ID NO: 4 are the pair of primers for FGA;
a primer consisting of SEQ ID NO: 5 and a fluorescent dye label and a primer consisting of SEQ ID NO: 6 are the pair of primers for D9S747;
a primer consisting of SEQ ID NO: 13 and a fluorescent dye label and a primer consisting of SEQ ID NO: 14 are the pair of primers for MBP;
a primer consisting of SEQ ID NO: 11 and a fluorescent dye label and a primer consisting of SEQ ID NO: 12 are the pair of primers for D9S162;
a primer consisting of SEQ ID NO: 17 and a fluorescent dye label and a primer consisting of SEQ ID NO: 18 are the pair of primers for THO1;
a primer consisting of SEQ ID NO: 19 and a fluorescent dye label and a primer consisting of SEQ ID NO: 20 are the pair of primers for IFN-A;
a primer consisting of SEQ ID NO: 21 and a fluorescent dye label and a primer consisting of SEQ ID NO: 22 are the pair of primers for D21S1245; and/or
a primer consisting of SEQ ID NO: 23 and a fluorescent dye label and a primer consisting of SEQ ID NO: 24 are the pair of primers for D20S48.

22. The method of claim 21, wherein:
the 5' end of the primers having a nucleotide sequence consisting of SEQ ID NO: 3, 5, and 21 are labelled with VIC;
the 5' end of the primers having a nucleotide sequence consisting of SEQ ID NO: 11, 17, 23 are labelled with NED;
the 5' end of the primer having a nucleotide sequence consisting of SEQ ID NO: 13 is labelled with 6-FAM; and/or
the 5' end of the primer having a nucleotide sequence consisting of SEQ ID NO: 19 is labelled with PET.

23. The method of claim 2, wherein the amplification of the set of microsatellite markers comprises three multiplex amplification reactions.

24. The method of claim 11, wherein the amplification of the set of markers comprises three multiplex amplification reactions.

* * * * *

```
                            SEQUENCE LISTING

<160> NUMBER OF SEQ ID NOS: 28

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
tcagtctctc tttctccttg ca                                                22

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
taggagcctg tggtcctgtt                                                   20

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
gacatcttaa ctggcattca tgg                                               23

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
cttctcagat cctctgacac tcg                                               23

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
gccattattg actctggaaa agac                                              24

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
```

-continued caggctctca aaatatgaac aaaat                                           25

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
acctaggcca tgttcacagc                                                 20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gagcagaatg agaggccaag                                                 20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ctgggcaaca agagcaaaat                                                 20

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
tttgttgttg ttcattgact tcagtc                                          26

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
gcaaccattt atgtggttag gg                                              22

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tcccacaaca aatctcctca c                                               21

<210> SEQ ID NO 13
<211> LENGTH: 23
<212> TYPE: DNA

```
<213> ORGANISM: Artificial Sequence
<220> FEATURE:
<223> OTHER INFORMATION: Primer

<400> SEQUENCE: 13
ggacctcgtg aattacaatc act                                          23

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
atccatttac ctacctgttc atcc                                         24

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gggcaacaag gagagactct                                              20

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
aaaaaaggac ctgcctttat cc                                           22

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
aggctctagc agcagctcat                                              20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tgtacacagg gcttccgagt                                              20

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
tgcgcgttaa gttaattggt t                                            21
```

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gtaaggtgga aaccccccact                                              20

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
ccagaaaatg acacatgaag ga                                            22

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
ttgttgagga tttttgcatc a                                             21

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
atggtctcca gtcccatctg                                               20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gcctgcacac aagaatatgt                                               20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
tctgtctgct gcctcctaca                                               20

<210> SEQ ID NO 26
<211> LENGTH: 22
<212> TYPE: DNA
<213> ORGANISM: Artificial Sequence
<220> FEATURE:

```
<223> OTHER INFORMATION: Primer

<400> SEQUENCE: 26
gatcctattt ttcttggggc ta                                              22

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ggcaacaaga gcaaaactcc                                                 20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ggtgctctct gccctatctg                                                 20
```